United States Patent
Diaz et al.

(10) Patent No.: US 10,585,075 B2
(45) Date of Patent: *Mar. 10, 2020

(54) SYSTEM FOR COLLECTING LIQUID SAMPLES

(71) Applicant: Elemental Scientific, Inc., Omaha, NE (US)

(72) Inventors: David Diaz, Omaha, NE (US); Jonathan Hein, Bennington, NE (US); Kyle W. Uhlmeyer, Omaha, NE (US); Daniel R. Wiederin, Omaha, NE (US); Tyler Yost, Omaha, NE (US); Kevin Wiederin, Omaha, NE (US)

(73) Assignee: ELEMENTAL SCIENTIFIC, INC., Omaha, NE (US)

(*) Notice: Subject to any disclaimer, the term of this patent is extended or adjusted under 35 U.S.C. 154(b) by 307 days.

This patent is subject to a terminal disclaimer.

(21) Appl. No.: 15/192,464

(22) Filed: Jun. 24, 2016

(65) Prior Publication Data

US 2016/0305917 A1 Oct. 20, 2016

Related U.S. Application Data

(63) Continuation-in-part of application No. PCT/US2015/018177, filed on Feb. 27, 2015.

(Continued)

(51) Int. Cl.
  *G01N 30/78* (2006.01)
  *G01N 30/06* (2006.01)

(52) U.S. Cl.
  CPC ............. *G01N 30/78* (2013.01); *G01N 30/06* (2013.01)

(58) Field of Classification Search
  CPC .......................... G01N 30/78; G01N 35/1097
  See application file for complete search history.

(56) References Cited

U.S. PATENT DOCUMENTS 3,241,432 A * 3/1966 Skeggs .................. G01N 35/08
                                                        250/576
3,834,227 A * 9/1974 Patterson ................ E21B 47/10
                                                        73/152.42

(Continued)

FOREIGN PATENT DOCUMENTS

CN      101881376 A    11/2010
EP        0163976 A1   12/1985

(Continued)

OTHER PUBLICATIONS

International Search Report dated Jun. 4, 2015 for PCT/US2015/018177.

(Continued)

*Primary Examiner* — John Fitzgerald
(74) *Attorney, Agent, or Firm* — Kevin E. West; Advent, LLP

(57) ABSTRACT

Systems and methods are described to determine whether a sample transmitted through a transfer line from a remote sampling system contains a suitable sample to analyze by an analysis system. A system embodiment includes, but is not limited to, a sample receiving line configured to receive a liquid segment a first detector configured to detect the liquid segment at a first location in the sample receiving line; a second detector configured to detect the liquid segment at a second location in the sample receiving line downstream from the first location; and a controller configured to register a continuous liquid segment in the sample receiving line when the first detector and the second detector match detection states prior to the controller registering a change of state of the first detector.

16 Claims, 15 Drawing Sheets

Related U.S. Application Data

(60) Provisional application No. 62/277,241, filed on Jan. 11, 2016, provisional application No. 62/276,705, filed on Jan. 8, 2016, provisional application No. 62/185,239, filed on Jun. 26, 2015, provisional application No. 61/946,256, filed on Feb. 28, 2014, provisional application No. 61/945,264, filed on Feb. 27, 2014.

(56) References Cited

U.S. PATENT DOCUMENTS

| | | | | |
|---|---|---|---|---|
| 4,100,797 | A * | 7/1978 | Oberhardt | G01F 1/704 73/861 |
| 4,114,144 | A * | 9/1978 | Hyman | A61M 5/365 128/DIG. 13 |
| 4,151,086 | A | 4/1979 | Brooks | |
| 4,210,809 | A * | 7/1980 | Pelavin | G01F 1/7086 250/343 |
| 4,366,384 | A * | 12/1982 | Jensen | A61M 5/365 250/575 |
| 4,752,690 | A * | 6/1988 | James | A61M 1/3626 250/341.5 |
| 4,797,191 | A | 1/1989 | Metzner et al. | |
| 5,260,665 | A * | 11/1993 | Goldberg | G01N 22/00 324/636 |
| 5,504,010 | A | 4/1996 | Mitani et al. | |
| 5,654,551 | A * | 8/1997 | Watt | G01F 1/7042 250/356.1 |
| 5,708,220 | A | 1/1998 | Burge | |
| 6,241,950 | B1 | 6/2001 | Veelenturf et al. | |
| 6,408,679 | B1 * | 6/2002 | Kline-Schoder | A61B 8/08 73/19.03 |
| 6,561,046 | B1 | 5/2003 | Taylor et al. | |
| 7,661,294 | B2 * | 2/2010 | Dam | A61M 1/3626 250/343 |
| 7,805,978 | B2 * | 10/2010 | Riley | A61M 5/365 73/19.03 |
| 7,818,992 | B2 * | 10/2010 | Riley | A61M 5/365 73/19.03 |
| 7,905,099 | B2 * | 3/2011 | Justak | F25B 49/005 250/574 |
| 7,981,082 | B2 * | 7/2011 | Wang | A61M 5/365 604/122 |
| 8,119,065 | B2 | 2/2012 | Bowers et al. | |
| 8,225,639 | B2 * | 7/2012 | Riley | A61M 5/365 73/19.03 |
| 9,283,332 | B2 * | 3/2016 | Unverdorben | A61M 5/365 |
| 2001/0037674 | A1 * | 11/2001 | Petro | B01D 15/08 73/61.52 |
| 2002/0064880 | A1 * | 5/2002 | Merten | B67C 3/206 436/43 |
| 2003/0092393 | A1 | 5/2003 | Tokhtuev et al. | |
| 2003/0138357 | A1 | 7/2003 | Adolfsen | |
| 2005/0087027 | A1 | 4/2005 | Widmer | |
| 2005/0123970 | A1 | 6/2005 | Ozbal et al. | |
| 2005/0194318 | A1 | 9/2005 | Ozbal et al. | |
| 2006/0021419 | A1 * | 2/2006 | Cassidy | A61M 5/1411 73/19.01 |
| 2008/0302178 | A1 * | 12/2008 | Karg | G01F 13/006 73/199 |
| 2012/0132013 | A1 | 5/2012 | Glatz et al. | |
| 2014/0165703 | A1 * | 6/2014 | Wilt | G01N 29/02 73/24.06 |
| 2016/0131617 | A1 * | 5/2016 | Burnett | G01N 30/32 73/61.56 |
| 2016/0370262 | A1 | 12/2016 | Diaz et al. | |
| 2018/0180639 | A1 * | 6/2018 | Diaz | G01N 35/1097 |

FOREIGN PATENT DOCUMENTS

| | | |
|---|---|---|
| EP | 0276304 A4 | 4/1990 |
| EP | 0276304 B1 | 6/1992 |
| JP | H03073860 | 3/1991 |
| JP | 2005531009 A | 10/2005 |
| JP | 2007512515 A | 5/2007 |
| WO | 9911373 A2 | 3/1999 |
| WO | 2004003522 A1 | 1/2004 |
| WO | 2005048126 A2 | 5/2005 |

OTHER PUBLICATIONS

International Search Report dated Oct. 7, 2016 for PCT/US2016/039327.

Chinese Office Action for Application No. 201580016642.3 dated Aug. 23, 2018.

International Preliminary Report on Patentability for Application No. PCT/US2015/018177 dated Aug. 30, 2016.

Office Action for Chinese Application No. 201580016642.3, dated Apr. 15, 2019.

Office Action for Japanese Application No. 2016-572370, dated Feb. 26, 2019.

Written Opinion dated Jun. 4, 2015 for International Application No. PCT/US2015/018177.

Office Action for Chinese Application No. 201680037720.2, dated Dec. 16, 2019.

\* cited by examiner

SYSTEM FOR COLLECTING LIQUID SAMPLES

CROSS-REFERENCE TO RELATED APPLICATIONS

The present application claims the benefit under 35 U.S.C. § 119(e) of U.S. Provisional Application Ser. No. 62/185,239, filed Jun. 26, 2015, and titled "SYSTEM FOR COLLECTING LIQUID SAMPLES," U.S. Provisional Application Ser. No. 62/276,705, filed Jan. 8, 2016, and titled "SYSTEM FOR COLLECTING LIQUID SAMPLES FROM A DISTANCE FOR MULTIPLE ANALYZERS," and U.S. Provisional Application Ser. No. 62/277,241, filed Jan. 11, 2016, and titled "SYSTEM FOR COLLECTING LIQUID SAMPLES FROM A DISTANCE FOR MULTIPLE ANALYZERS." The present application is also a continuation-in-part of International Application No. PCT/US2015/018177, filed Feb. 27, 2015, and titled "SYSTEM FOR COLLECTING LIQUID SAMPLES FROM A DISTANCE," which claims the benefit under 35 U.S.C. § 119(e) of U.S. Provisional Application Ser. No. 61/945,264, filed Feb. 27, 2014, and titled "SAMPLE ANALYSIS SYSTEM OPERABLE OVER LONG DISTANCES" and U.S. Provisional Application Ser. No. 61/946,256, filed Feb. 28, 2014, and titled "SAMPLE ANALYSIS SYSTEM OPERABLE OVER LONG DISTANCES". U.S. Provisional Application Ser. Nos. 61/945,264, 61/946,256, 62/185,239, 62/276,705, and 62/277,241, and International Application No. PCT/US15/18177 are herein incorporated by reference in their entireties.

BACKGROUND

In many laboratory settings, it is often necessary to analyze a large number of chemical or biological samples at one time. In order to streamline such processes, the manipulation of samples has been mechanized. Such mechanized sampling can be referred to as autosampling and can be performed using an automated sampling device, or autosampler.

Inductively Coupled Plasma (ICP) spectrometry is an analysis technique commonly used for the determination of trace element concentrations and isotope ratios in liquid samples. ICP spectrometry employs electromagnetically generated partially ionized argon plasma which reaches a temperature of approximately 7,000K. When a sample is introduced to the plasma, the high temperature causes sample atoms to become ionized or emit light. Since each chemical element produces a characteristic mass or emission spectrum, measuring the spectra of the emitted mass or light allows the determination of the elemental composition of the original sample.

Sample introduction systems may be employed to introduce the liquid samples into the ICP spectrometry instrumentation (e.g., an Inductively Coupled Plasma Mass Spectrometer (ICP/ICP-MS), an Inductively Coupled Plasma Atomic Emission Spectrometer (ICP-AES), or the like), or other sample detector or analytic instrumentation for analysis. For example, a sample introduction system may withdraw an aliquot of a liquid sample from a container and thereafter transport the aliquot to a nebulizer that converts the aliquot into a polydisperse aerosol suitable for ionization in plasma by the ICP spectrometry instrumentation. The aerosol is then sorted in a spray chamber to remove the larger aerosol particles. Upon leaving the spray chamber, the aerosol is introduced into the plasma by a plasma torch assembly of the ICP-MS or ICP-AES instruments for analysis.

SUMMARY

Systems and methods are described to determine whether a sample transmitted through a transfer line from a remote sampling system contains a suitable sample to analyze by an analysis system. A system embodiment includes, but is not limited to, a sample receiving line configured to receive a liquid segment a first detector configured to detect the liquid segment at a first location in the sample receiving line; a second detector configured to detect the liquid segment at a second location in the sample receiving line downstream from the first location; and a controller configured to register a continuous liquid segment in the sample receiving line when the first detector and the second detector match detection states prior to the controller registering a change of state of the first detector.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. Any dimensions included in the accompanying figures are provided by way of example only and are not meant to limit the present disclosure.

DETAILED DESCRIPTION

Figure 1:
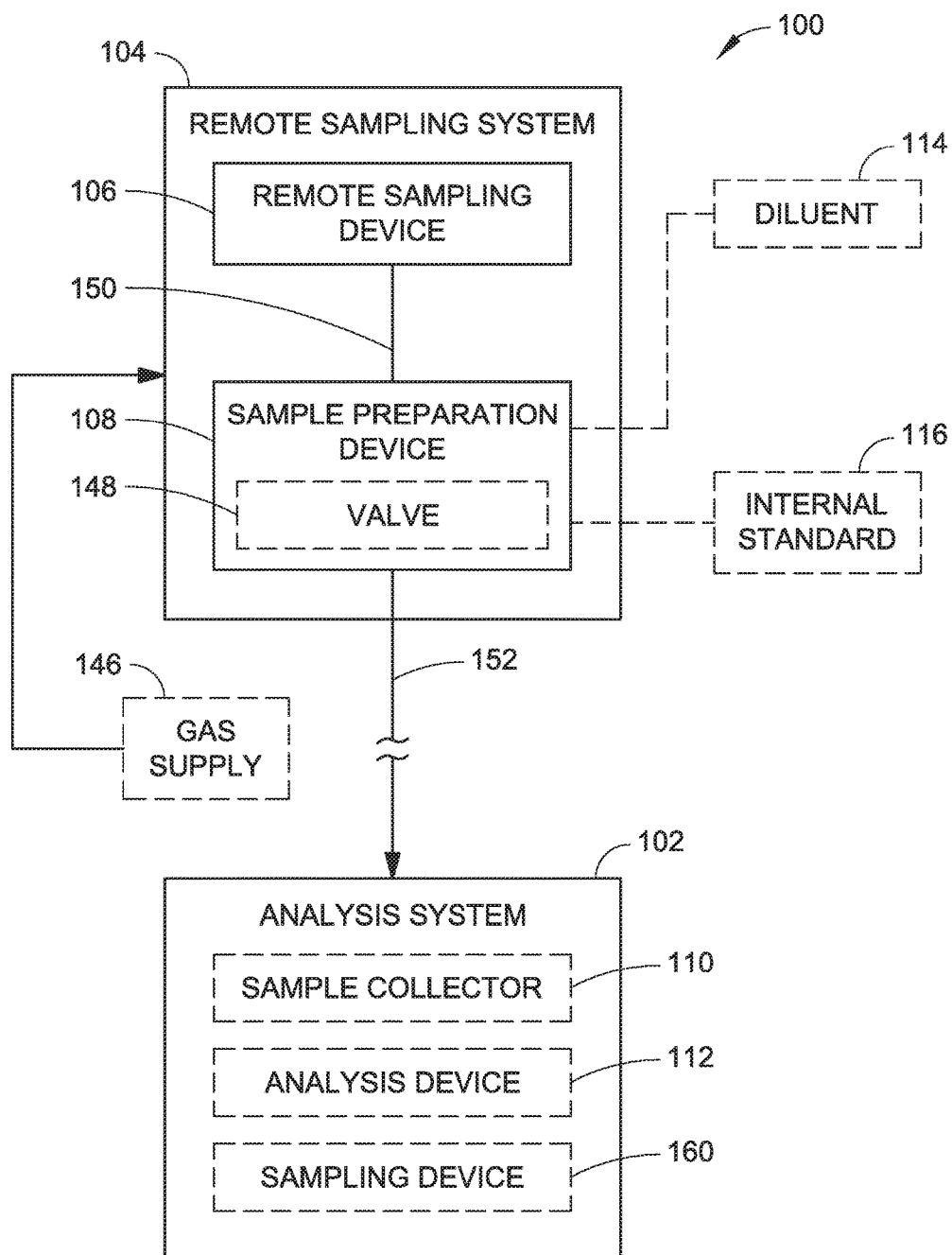
FIG. 1 is a partial line diagram illustrating a system configured to analyze samples transported over long distances in accordance with example embodiments of the present disclosure.
Figure 2A:
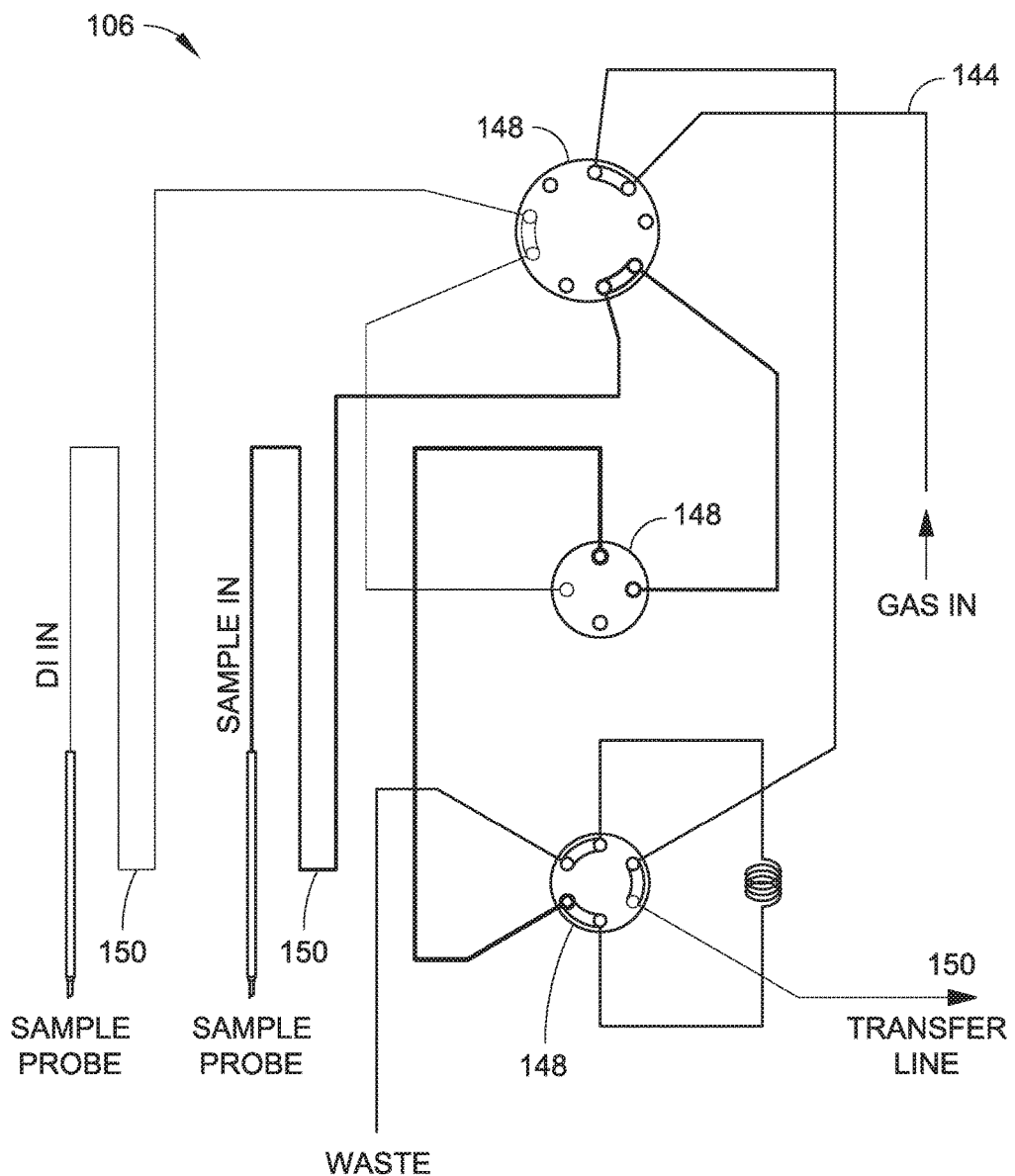
FIG. 2A is an environmental view illustrating a remote sampling device used in a remote sampling system, in accordance with example embodiments of the present disclosure.
Figure 2B:
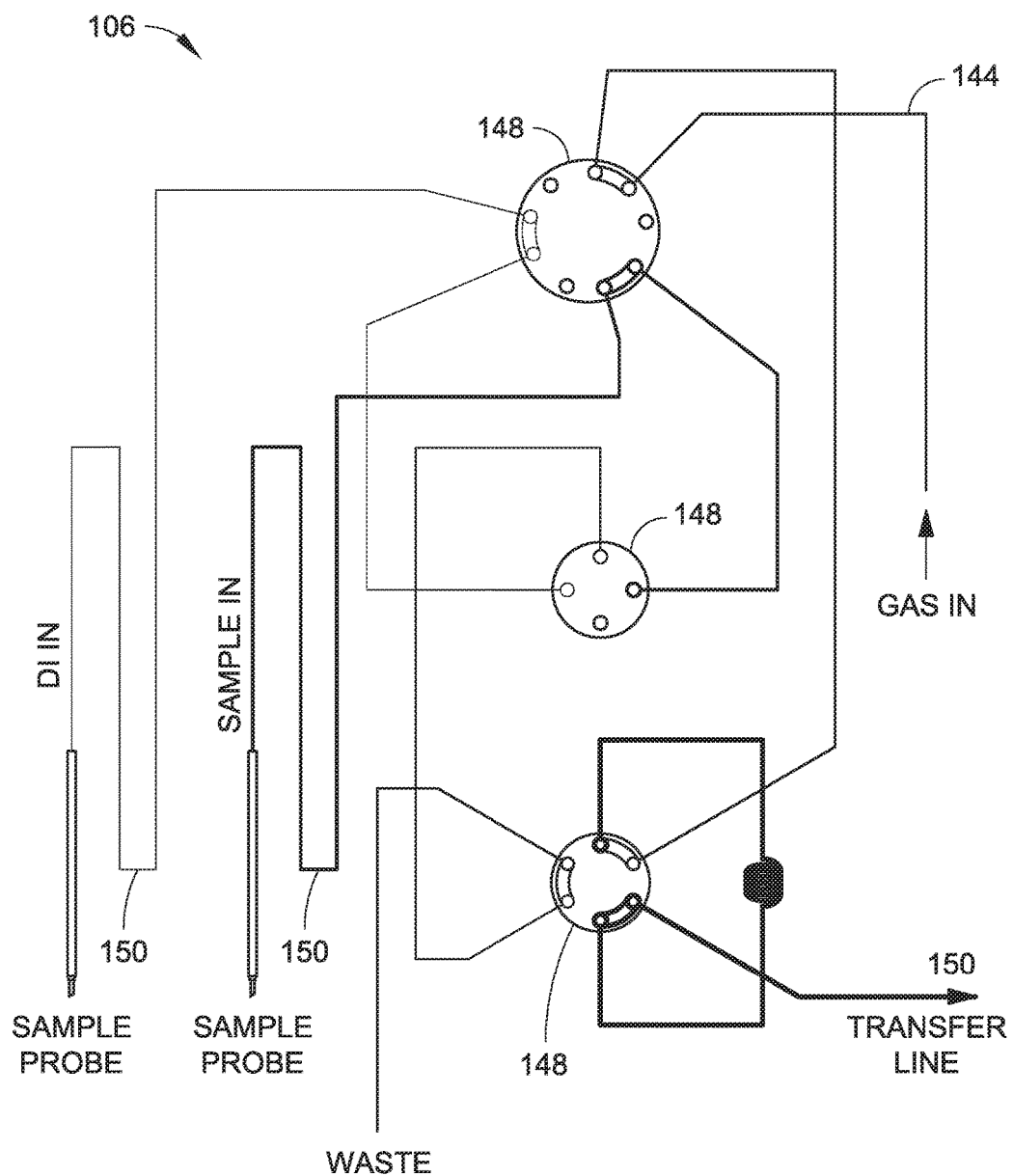
FIG. 2B is an environmental view illustrating a remote sampling device used in a remote sampling system, in accordance with example embodiments of the present disclosure.
Figure 3A:
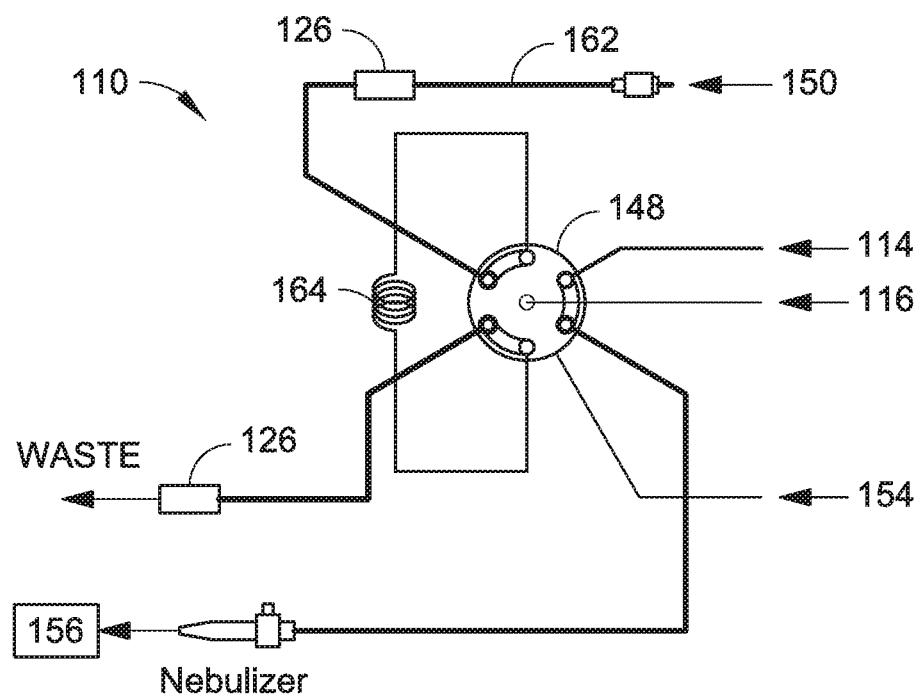
FIG. 3A is an environmental view illustrating an analysis device used in an analysis system, in accordance with example embodiments of the present disclosure.
Figure 3B:
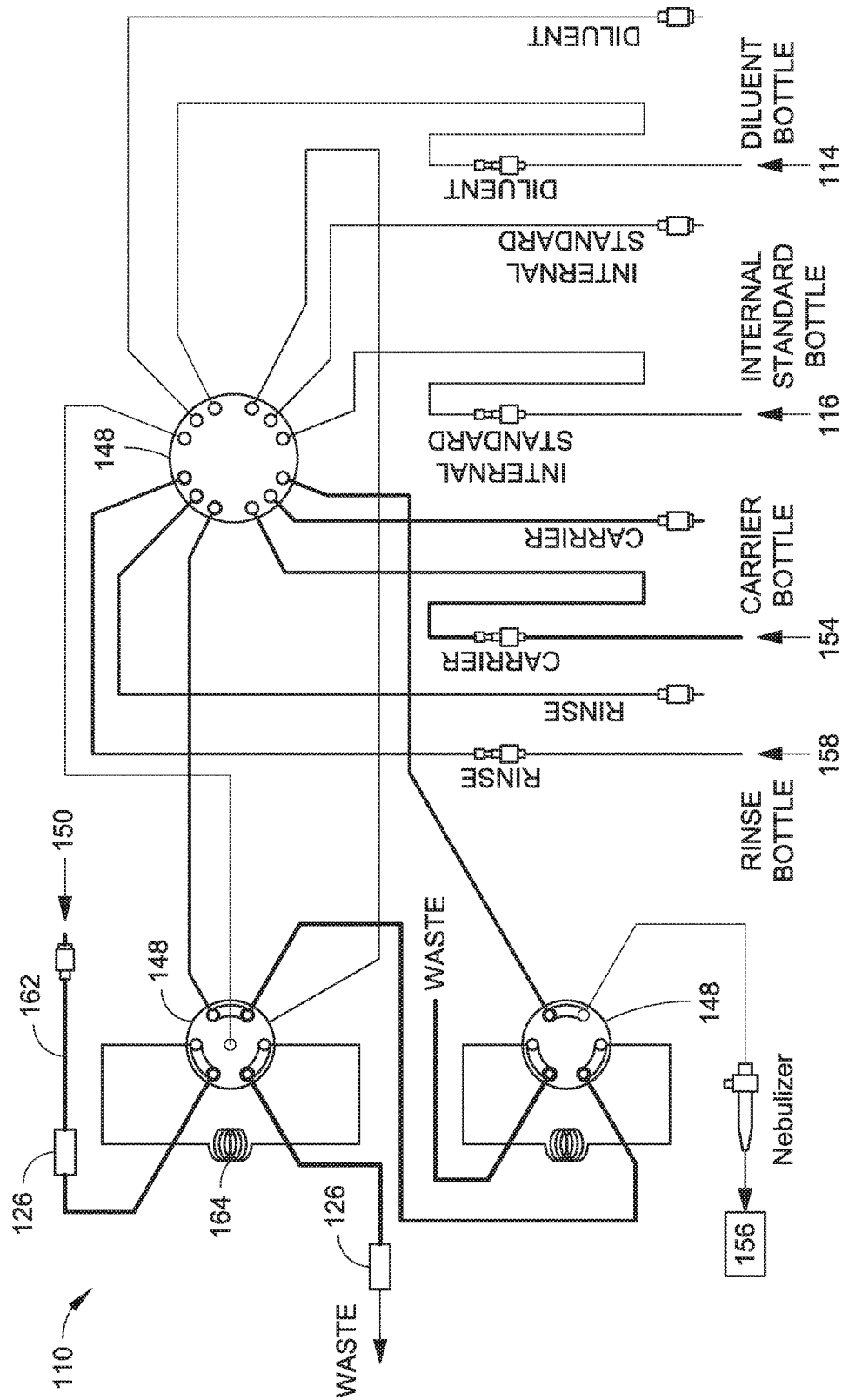
FIG. 3B is an environmental view illustrating an analysis device used in an analysis system, in accordance with example embodiments of the present disclosure.
Figure 4:
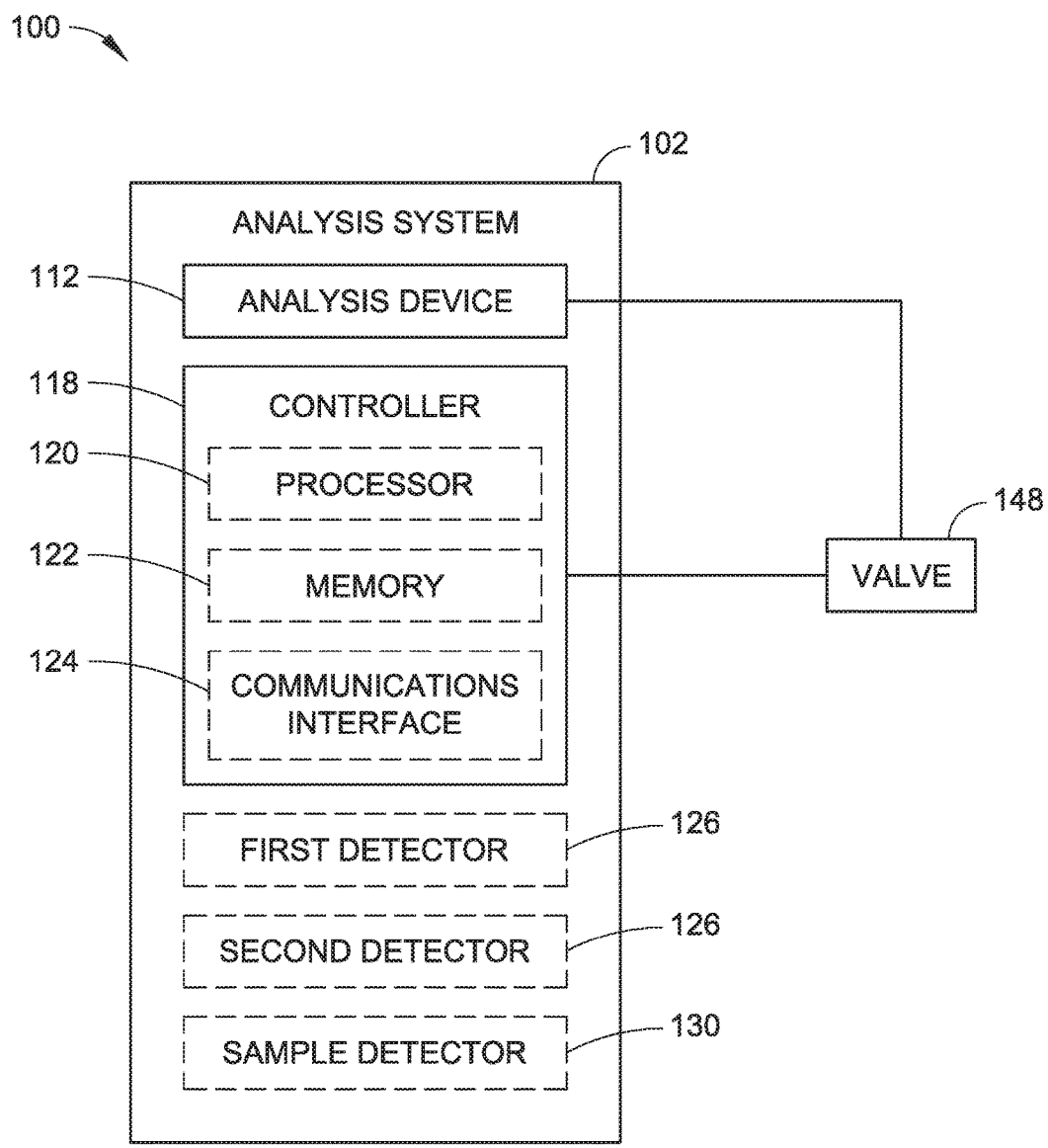
FIG. 4 is a partial line diagram illustrating an analysis system within the system configured to analyze samples transported over long distances in accordance with example embodiments of the present disclosure.
Figure 5:
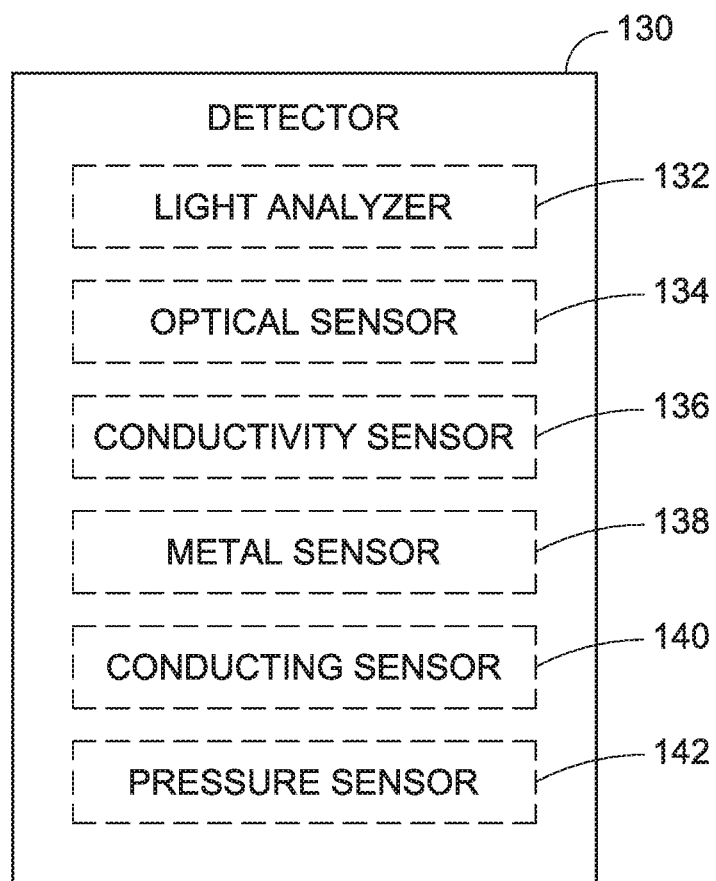
FIG. 5 is a partial line diagram illustrating a detector that can be utilized within the analysis system shown in FIG. 4 in accordance with example embodiments of the present disclosure.

Referring generally to FIGS. 1 through 13, example systems configured to analyze samples transported over long distances are described. In example embodiments, one or more samples can be analyzed by multiple analysis systems, where such analysis systems can comprise differing analysis techniques. A system 100 includes an analysis system 102 at a first location. The system 100 can also include one or more remote sampling systems 104 at a second location remote from the first location. For instance, the one or more remote sampling systems 104 can be positioned proximate a source of chemical, such as a chemical storage tank, a chemical treatment tank (e.g., a chemical bath), a chemical transport line or pipe, or the like (e.g., the second location), to be analyzed by the analysis system 102, where the analysis system 102 can be positioned remote from the remote sampling system(s) 104, such as an analysis hub for a production facility (e.g., the first location). The system 100 can also include one or more remote sampling system(s) 104 at a third location, a fourth location, and so forth, where the third location and/or the fourth location are remote from the first location. In implementations, the third location, the fourth location, and other locations of the remote sampling systems 104 can be remote from respective other locations of other remote sampling systems 104. For example, one remote sampling system 104 can be positioned at a water line (e.g., a deionized water transport line), whereas one or more other remote sampling systems 104 can be positioned at a chemical storage tank, a chemical treatment tank (e.g., a chemical bath), a chemical transport line or pipe, or the like. In some embodiments, the system 100 also may include one or more remote sampling system(s) 104 at the first location (e.g., proximate to the analysis system 102). For example, a sampling system 104 at the first location may include an autosampler coupled with the analysis system 102. The one or more sampling systems 104 can be operable to receive samples from the first location, the second location, the third location, the fourth location, and so forth, and the system 100 can be operable to deliver the samples to the analysis system 102 for analysis.

A remote sampling system 104 can be configured to receive a sample 150 and prepare the sample 150 for delivery (e.g., to the analysis system 102) and/or analysis. In embodiments, the remote sampling system 104 can be disposed various distances from the analysis system 102 (e.g., 1 m, 5 m, 10 m, 30 m, 50 m, 100 m, 300 m, 1000 m, etc.). In implementations, the remote sampling system 104 can include a remote sampling device 106 and a sample preparation device 108. The sample preparation device 108 may further include a valve 148, such as a flow-through valve. In implementations, the remote sampling device 106 can include a device configured for collecting a sample 150 from a sample stream or source (e.g., a liquid, such as waste water, rinse water, chemical, industrial chemical, etc., a gas, such as an air sample and/or contaminants therein to be contacted with a liquid, or the like). The remote sampling device 106 can include components, such as pumps, valves, tubing, sensors, etc., suitable for acquiring the sample from the sample source and delivering the sample over the distance to the analysis system 102. The sample preparation device 108 can include a device configured to prepare a collected sample 150 from the remote sampling device 106 using a diluent 114, an internal standard 116, a carrier 154, etc., such as to provide particular sample concentrations, spiked samples, calibration curves, or the like, and can rinse with a rinse solution 158.

In some embodiments, a sample 150 may be prepared (e.g., prepared sample 152) for delivery and/or analysis using one or more preparation techniques, including, but not necessarily limited to: dilution, pre-concentration, the addition of one or more calibration standards, and so forth. For example, a viscous sample 150 can be remotely diluted (e.g., by sample preparation device 108) before being delivered to the analysis system 102 (e.g., to prevent the sample 150 from separating during delivery). As described herein, a sample that has been transferred from the remote sampling system 104 can be referred to as a sample 150, where sample 150 can also refer to a prepared sample 152. In some embodiments, sample dilution may be dynamically adjusted (e.g., automatically adjusted) to move sample(s) 150 through the system at a desired rate. For instance, diluent 114 added to a particular sample or type of sample is increased when a sample 150 moves through the system 100 too slowly (e.g., as measured by the transfer time from the second location to the first location). In another example, one liter (1 L) of seawater can be remotely pre-concentrated before delivery to the analysis system 102. In a further example, electrostatic concentration is used on material from an air sample to pre-concentrate possible airborne contaminants. In some embodiments, in-line dilution and/or calibration is automatically performed by the system 100. For instance, a sample preparation device 108 can add one or more internal standards to a sample delivered to the analysis system 102 to calibrate the analysis system 102.

In embodiments of the disclosure, the analysis system 102 can include a sample collector 110 and/or sample detector 130 configured to collect a sample 150 from a sample transfer line 144 coupled between the analysis system 102 and one or more remote sampling systems 104. The sample collector 110 and/or the sample detector 130 can include components, such as pumps, valves, tubing, ports, sensors, etc., to receive the sample 150 from one or more of the remote sampling systems 104 (e.g., via one or more sample transfer lines 144). For example, where the system 100 includes multiple remote sampling systems 104, each remote sampling system can include a dedicated sample transfer line 144 to couple to a separate portion of the sample collector 110 or to a separate sample collector 110 of the analysis system 102. Additionally, the analysis system 102 may include a sampling device 160 configured to collect a sample 150 that is local to the analysis system 102 (e.g., a local autosampler).

Figure 6:
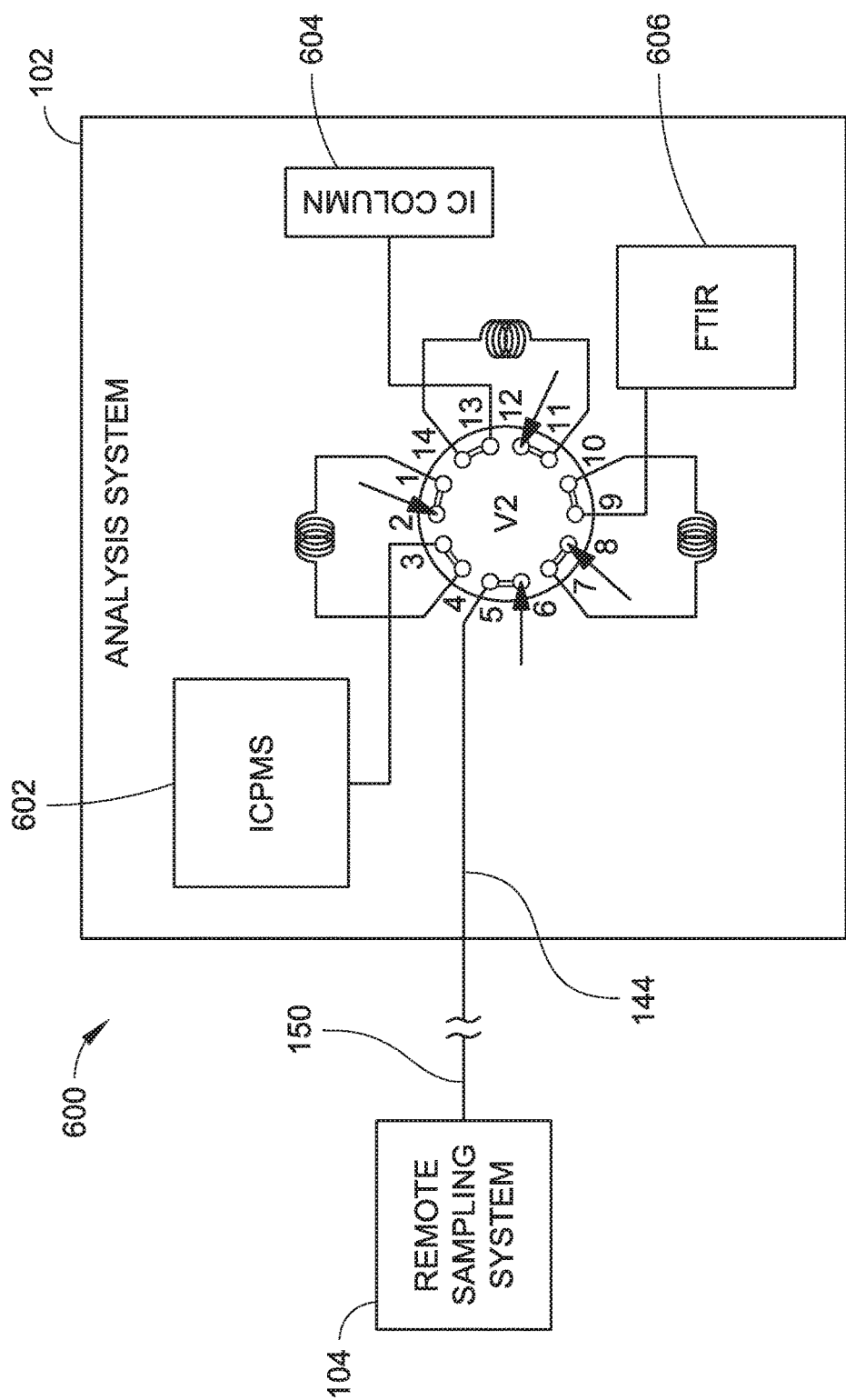
FIG. 6 is an environmental view illustrating an analysis system having a plurality of analysis devices to analyze a sample received from a remote sampling system in accordance with example embodiments of the present disclosure.

The analysis system 102 also includes at least one analysis device 112 configured to analyze samples to determine trace element concentrations, isotope ratios, and so forth (e.g., in liquid samples). For example, the analysis device 112 can include ICP spectrometry instrumentation including, but not limited to, an Inductively Coupled Plasma Mass Spectrometer (ICP/ICP-MS), an Inductively Coupled Plasma Atomic Emission Spectrometer (ICP-AES), or the like. In embodiments, the analysis system 102 includes a plurality of analysis devices 112 (i.e., more than one analysis device). For example, the system 100 and/or the analysis system 102 can include multiple sampling loops, with each sampling loop introducing a portion of the sample to the plurality of analysis devices 112. As another example, the system 100 and/or the analysis system 102 can be configured with a multiposition valve, such that a single sample can be rapidly and serially introduced to the plurality of analysis devices 112. For example, FIG. 6 shows one remote sampling system 104 in fluid communication with the analysis system 102, wherein the analysis system 102 includes a multiposition valve 600 coupled with three analysis devices (shown as ICPMS 602, ion chromatograph (IC) Column 604, and Fourier transform infrared spectroscop (FTIR) 606) for analysis of the sample received from the remote sampling system 104. While FIG. 6 shows an embodiment where the analysis system 102 includes three analysis devices, the analysis system 102 can include fewer (e.g., less than three) or more (e.g., more than three) analysis devices 112. In embodiments, the analysis devices 112 can include, but are not limited to, ICPMS (e.g., for trace metal determinations), ICPOES (e.g., for trace metal determinations), ion chromatograph (e.g., for anion and cation determinations), liquid chromatograph (LC) (e.g., for organic contaminants determinations), FTIR infrared (e.g., for chemical composition and structural information determinations), particle counter (e.g., for detection of undissolved particles), moisture analyzer (e.g., for detection of water in samples), gas chromatograph (GC) (e.g., for detection of volatile components), or the like. In embodiments, the plurality of analysis devices 112 can be located at the same location as the remote sampling device 104, while the system 100 can include one or more additional analysis devices 112 located remotely from the remote sampling system 104 for additional or differing sample analysis than those analys(es) performed by the plurality of analysis devices 112. Alternatively or additionally, the plurality of analysis devices 112 can be located at a different location than the remote sampling system 104.

The system 100 and/or analysis system 102 can be configured to report analyte concentration at a location over time (shown further below with reference to FIG. 13). In some embodiments, the analysis device 112 may be configured to detect one or more trace metals in a sample 150. In other embodiments, the analysis device 112 may be configured for ion chromatography. For example, ions and/or cations can be collected in a sample 150 and delivered to a chromatograph analysis device 112. In further embodiments, organic molecules, proteins, and so on, can be collected in samples and delivered to a high resolution time-of-flight (HR-ToF) mass spectrometer analysis device 112 (e.g., using a nebulizer 156). Thus, systems as described herein can be used for various applications, including, but not necessarily limited to: pharmaceutical applications (e.g., with a central mass spectrometer analysis device connected to multiple pharmaceutical reactors), waste monitoring of one or more waste streams, semiconductor fabrication facilities, and so forth. For example, a waste stream may be continuously monitored for contaminants and diverted to a tank when a contaminant is detected. As another example, one or more chemical streams can be continuously monitored via analysis of the samples obtained by one or more of the remote sampling systems 104 linked to the analysis system 102, whereby a contamination limit can be set for each of the chemical streams. Upon detection of a contaminant exceeding the contamination limit for a particular stream, the system 100 can provide an alert.

The remote sampling system 104 can be configured to selectively couple with at least one sample transfer line 144 so that the remote sampling system 104 is operable to be in fluid communication with the sample transfer line 144 for supplying a continuous liquid sample segment 150 to the sample transfer line 144. For example, the remote sampling system 104 may be configured to collect a sample 150 and supply the sample 150 to the sample transfer line 144 using, for instance, a flow-through valve 148, coupling the remote sampling system 104 to the sample transfer line 144. The supply of the sample 150 to the sample transfer line 144 can be referred to as a "pitch." The sample transfer line 144 can be coupled with a gas supply 146 and can be configured to transport gas from the second location (and possibly the third location, the fourth location, and so forth) to the first location. In this manner, liquid sample segments supplied by the remote sampling system 104 are collected in a gas stream, and transported to the location of the analysis system 102 using gas pressure sample transfer.

In some embodiments, gas in the sample transfer line 144 can include an inert gas, including, but not necessarily limited to: nitrogen gas, argon gas, and so forth. In some embodiments, the sample transfer line 144 may include an unsegmented or minimally segmented tube having an inside diameter of eight-tenths of a millimeter (0.8 mm). However, an inside diameter of eight-tenths of a millimeter is provided by way of example only and is not meant to limit the present disclosure. In other embodiments, the sample transfer line 144 may include an inside diameter greater than eight-tenths of a millimeter and/or an inside diameter less than eight-tenths of a millimeter. In some embodiments, pressure in the sample transfer line 144 can range from at least approximately four (4) bar to ten (10) bar. However, this range is provided by way of example only and is not meant to limit the present disclosure. In other embodiments, pressure in the sample transfer line 144 may be greater than ten bar and/or less than four bar. Further, in some specific embodiments, the pressure in the sample transfer line 144 may be adjusted so that samples 150 are dispensed in a generally upward direction (e.g., vertically). Such vertical orientation can facilitate transfer of a sample collected at a location that is lower than the analysis system 102 (e.g., where sample source(s) and remote sampling system(s) are located "downstairs" relative to the analysis system 102).

In some examples, the sample transfer line 144 can be coupled with a remote sampling system 104 in fluid communication with a first liquid bath (or chemical bath) and an analysis system 102 in fluid communication with a second liquid bath (or chemical bath). In embodiments of the disclosure, the system 100 may include one or more leak sensors (e.g., mounted in a trough) to prevent or minimize overflow at the first location and/or one or more remote locations (e.g., the second location, the third location, the fourth location, and so forth). A pump, such as a syringe pump or a vacuum pump, may be used to load sample into the sampling device 106. A valve 148 may be used to select the sample 150 at the remote sampling system 104, and the sample 150 can be supplied to the sample transfer line 144, which can deliver the sample 150 to the analysis system 102 at the first location. Another pump, such as a diaphragm pump, may be used to pump a drain on the analysis system 102 and pull the sample 150 from the sample transfer line 144.

The system 100 can be implemented as an enclosed sampling system, where the gas and samples in the sample transfer line 144 are not exposed to the surrounding environment. For example, a housing and/or a sheath can enclose one or more components of the system 100. In some embodiments, one or more sample lines of the remote sampling system 104 may be cleaned between sample deliveries. Further, the sample transfer line 144 may be cleaned (e.g., using a cleaning solution) between samples 150.

Figure 7:
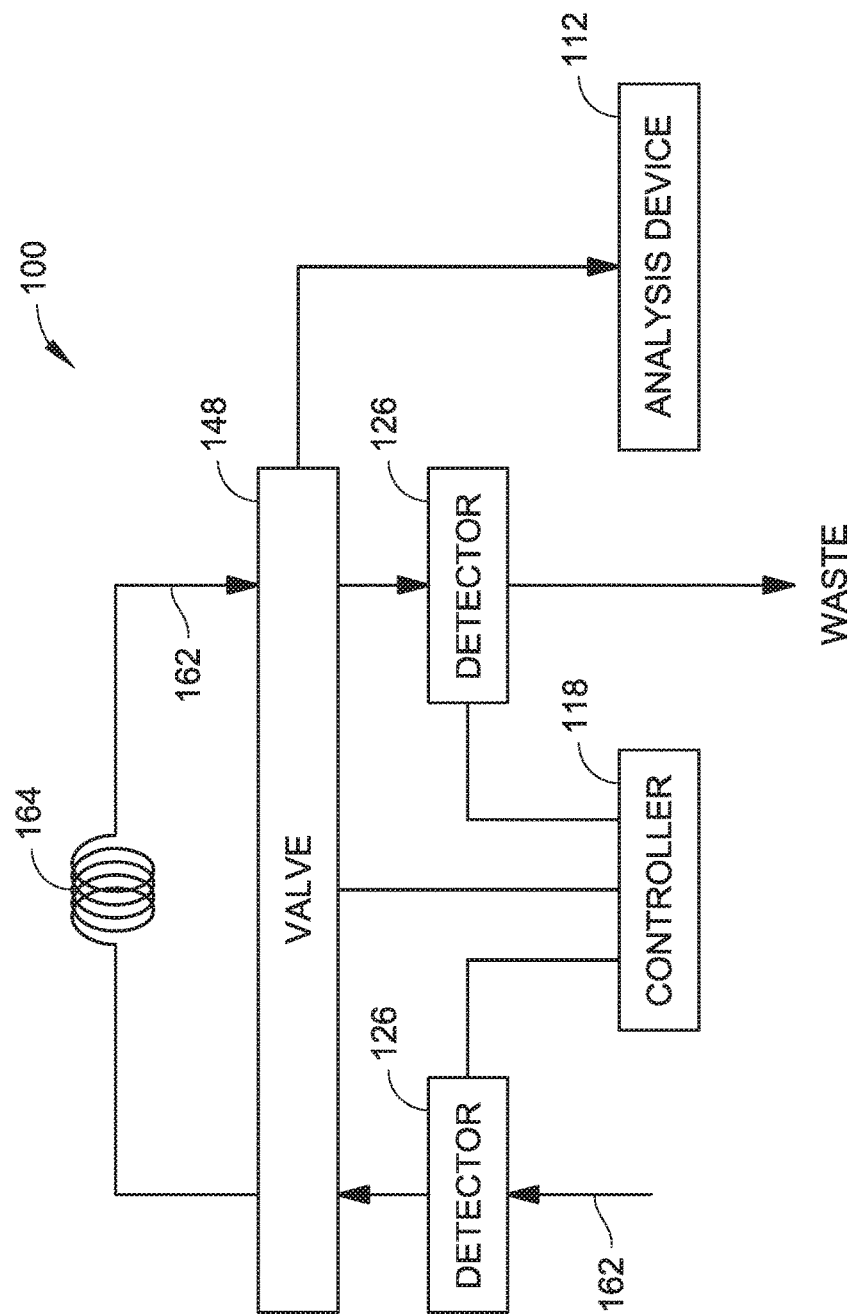
FIG. 7 is a diagrammatic illustration of a system including a sample receiving line and detectors configured to determine when the sample receiving line contains a continuous liquid segment between the detectors in accordance with example embodiments of the present disclosure.

The sample transfer line 144 can be configured to selectively couple with a sample receiving line 162 (e.g., a sample loop 164) at the first location so that the sample loop 164 is operable to be in fluid communication with the sample transfer line 144 to receive a continuous liquid sample segment. The delivery of the continuous liquid sample segment to the sample loop 164 can be referred to as a "catch." The sample loop 164 is also configured to selectively couple with the analysis device 112 so that the sample loop 164 is operable to be in fluid communication with the analysis device 112 to supply the continuous liquid sample segment to the analysis device 112 (e.g., when the system 100 has determined that a sufficient liquid sample segment is available for analysis by the analysis system 102). In embodiments of the disclosure, the analysis system 102 can include one or more detectors configured to determine that the sample loop 164 contains a sufficient amount of the continuous liquid sample segment for analysis by the analysis system 102. In one example, a sufficient amount of the continuous liquid sample can include enough liquid sample to send to the analysis device 112. Another example of a sufficient amount of the continuous liquid sample can include a continuous liquid sample in the sample receiving line 162 between a first detector 126 and a second detector 128 (e.g., as shown in FIG. 7). In implementations, the first detector 126 and/or the second detector 128 may include a light analyzer 132, an optical sensor 134, a conductivity sensor 136, a metal sensor 138, a conducting sensor 140, and/or a pressure sensor 142. It is contemplated that the first detector 126 and/or the second detector 128 may include other sensors. For example, the first detector 126 may include a light analyzer 132 that detects when the sample 150 enters the sample loop 164, and the second detector 128 may include another light analyzer 132 that detects when the sample loop 164 is filled. This example can be referred to as a "successful catch." It should be noted that the light analyzers 132 are provided by way of example only and are not meant to limit the present disclosure. Other example detectors include, but are not necessarily limited to: optical sensors, conductivity sensors, metal sensors, conducting sensors, pressure sensors, and so on.

Referring to FIG. 7, systems 100 are described that can determine when a continuous liquid sample segment is contained in a sample receiving line 162 and/or when a sample loop 164 contains a sufficient amount of the continuous liquid sample segment for analysis (e.g., by the analysis system 102). In example embodiments, a first detector 126 can be configured to determine two or more states, which can represent the presence of liquid (e.g., a liquid sample segment) at a first location in the sample receiving line 162, the absence of liquid at the first location in the sample receiving line 162, and so forth. For example, a first state (e.g., represented by a first logic level, such as a high state) can be used to represent the presence of a liquid sample segment at the first location in the sample receiving line 162 (e.g., proximate to the first detector 126), and a second state (e.g., represented by a second logic level, such as a low state) can be used to represent the absence of a liquid sample segment at the first location in the sample receiving line 162 (e.g., a void or gas in the sample receiving line 162).

In some embodiments, a first detector 126 comprising a pressure sensor 142 can be used to detect the presence of liquid at the first location in the sample receiving line 162 (e.g., by detecting an increase in pressure in the sample receiving line 162 proximate to the first location when liquid is present). The first detector 126 can also be used to detect the absence of liquid at the first location in the sample receiving line 162 (e.g., by detecting a decrease in pressure in the sample receiving line 162 proximate to the first location). However, a pressure sensor is provided by way of example and is not meant to limit the present disclosure. In other embodiments, a first detector 126 comprising an optical sensor 134 can be used to detect the presence of liquid at the first location in the sample receiving line 162 (e.g., by detecting a reduction in light passing through the sample receiving line 162 proximate to the first location when liquid is present). The first detector 126 can also be used to detect the absence of liquid at the first location in the sample receiving line 162 (e.g., by detecting an increase in light passing through the sample receiving line 162 proximate to the first location). In these examples, the first detector 126 can report the presence of liquid sample at the first location as a high state and the absence of liquid sample at the first location as a low state.

In some embodiments, a system 100 may also include one or more additional detectors, such as a second detector 126, a third detector, and so forth. For example, a second detector 126 can also be configured to determine two or more states, which can represent the presence of liquid (e.g., a liquid sample segment) at a second location in the sample receiving line 162, the absence of liquid at the second location in the sample receiving line 162, and so forth. For example, a first state (e.g., represented by a first logic level, such as a high state) can be used to represent the presence of a liquid sample segment at the second location in the sample receiving line 162 (e.g., proximate to the second detector 126), and a second state (e.g., represented by a second logic level, such as a low state) can be used to represent the absence of a liquid sample segment at the second location in the sample receiving line 162.

In some embodiments, a second detector 126 comprising a pressure sensor 142 can be used to detect the presence of liquid at the second location in the sample receiving line 162 (e.g., by detecting an increase in pressure in the sample receiving line 162 proximate to the second location when liquid is present). The second detector 126 can also be used to detect the absence of liquid at the second location in the sample receiving line 162 (e.g., by detecting a decrease in pressure in the sample receiving line 162 proximate to the second location). However, a pressure sensor is provided by way of example and is not meant to limit the present disclosure. In other embodiments, a second detector 126 comprising an optical sensor 134 can be used to detect the presence of liquid at the second location in the sample receiving line 162 (e.g., by detecting a reduction in light passing through the sample receiving line 162 proximate to the second location when liquid is present). The second detector 126 can also be used to detect the absence of liquid at the second location in the sample receiving line 162 (e.g., by detecting an increase in light passing through the sample receiving line 162 proximate to the second location). In these examples, the second detector 126 can report the presence of liquid sample at the second location as a high state and the absence of liquid sample at the second location as a low state.

A controller 118 can be communicatively coupled with one or more detector(s) 126 and configured to register liquid at the first location in the sample receiving line 162, the second location in the sample receiving line 162, another location in the sample receiving line 162, and so on. For example, the controller 118 initiates a detection operation using a first detector 126, and liquid at the first location in the sample receiving line 162 can be registered by the controller 118 (e.g., when the controller 118 registers a change of state from low to high as determined by the first detector 126). Then, the first detector 126 may be monitored (e.g., continuously, at least substantially continuously), and the controller 118 can subsequently register an absence of liquid at the first location in the sample receiving line 162 (e.g., when the controller 118 registers a change of state from high to low as determined by the first detector 126).

Similarly, the controller 118 can also initiate a detection operation using a second detector 126, and liquid at the second location in the sample receiving line 162 can be registered by the controller 118 (e.g., when the controller 118 registers a change of state from low to high as determined by the second detector 126). Then, the second detector 126 may be monitored (e.g., continuously, at least substantially continuously), and the controller 118 can subsequently register an absence of liquid at the second location in the sample receiving line 162 (e.g., when the controller 118 registers a change of state from high to low as determined by the second detector 126).

The controller 118 and/or one or more detectors 126 can include or influence the operation of a timer to provide timing of certain events (e.g., presence or absence of liquids at particular times at multiple locations in the sample receiving line 162) for the system 100. As an example, the controller 118 can monitor the times at which changes of state are registered by the various detector(s) in order to make determinations as to whether to allow the liquid sample to be directed to the analysis system 102 (e.g., as opposed to directing the liquid to waste or a holding loop). As another example, the controller 118 can monitor the time that a liquid spends in the sample receiving line 162 and/or the sample loop 164 based upon the change of states registered by the controller 118 via the detector(s) 126.

Liquid Sample Segment Interruption & Determination of Suitable Liquid Segment

Figure 8:
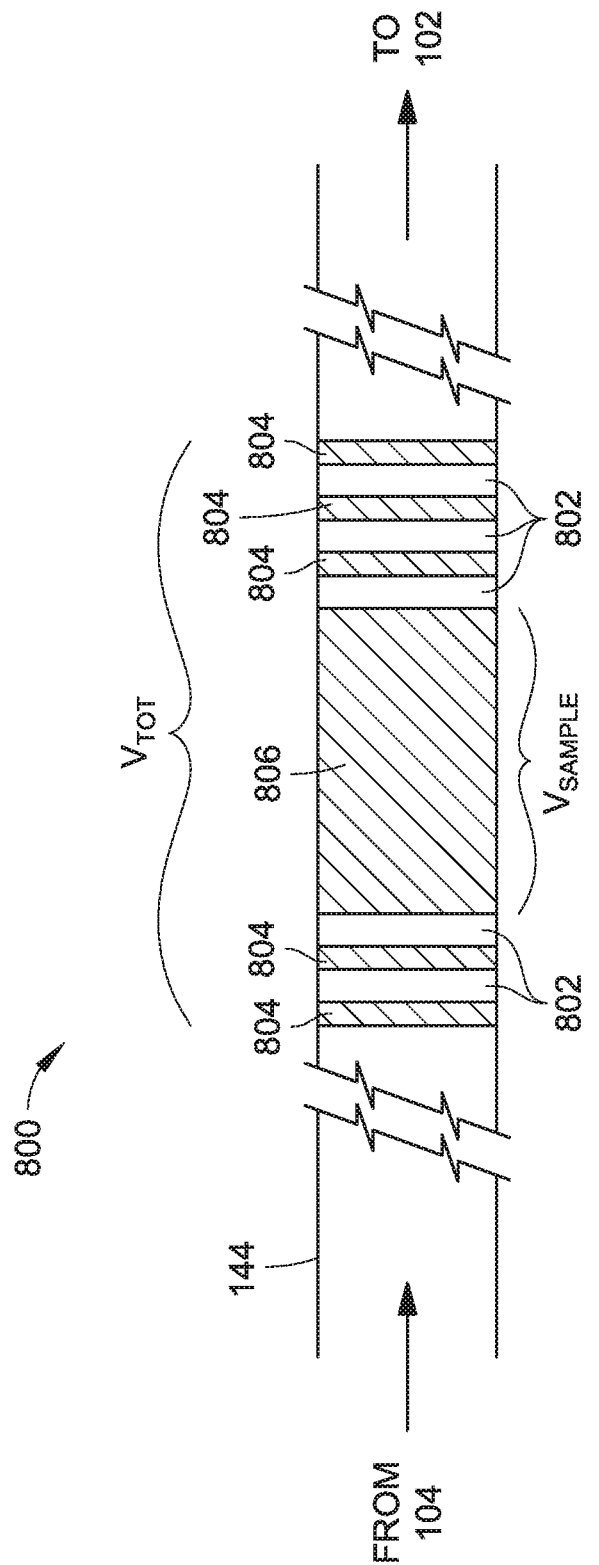
FIG. 8 is a partial cross section of a sample transfer line containing multiple segments of a sample obtained by a remote sampling system in accordance with example embodiments of the present disclosure.

Generally, when a sample is obtained proximate an associated analysis device (e.g., an autosampler next to an analysis device), the sample can span the entire distance between the sample source and the analysis device without requiring substantial sample amounts. However, for long-distance transfer of a sample, filling the entire transfer line 144 between with the remote sampling system 104 and the analysis system 102 (e.g., up to hundreds of meters of sample length) could be prohibitive or undesirable, such as due to environmental concerns with disposing unused sample portions, viscosity of the sample, or the like. Accordingly, in embodiments, the remote sampling system 104 does not fill the entire transfer line 144 with sample, rather, a liquid sample segment representing a fraction of the total transfer line 144 volume is sent through the transfer line 144 for analysis by the analysis system 102. For example, while the transfer line 144 can be up to hundreds of meters long, the sample may occupy about a meter or less of the transfer line 144 at any given time during transit to the analysis system 102. While sending liquid sample segments through the line can reduce the amount of sample sent from the remote sample systems 104, the sample can incur bubbles or gaps/voids in the sample transfer line 144 during transit to the analysis system 102. Such bubbles or gaps/voids can form due to circumstances associated with long-distance transfer of the sample such as changes in orifices between tubing during transit, due to interaction with residual cleaning fluid used to clean the lines between samples, due to reactions with residual fluid in the lines, due to pressure differential(s) along the span of transfer line, or the like. For example, as shown in FIG. 8, a liquid sample 800 can be sent from the remote sampling system 104 through the transfer line 144 to the first location where the analysis system 102 is located. The volume of the total sample obtained by the remote sampling system 104 is represented by $V_{TOT}$ in FIG. 8. As shown, gaps or voids 802 can form in the transfer line 144 during transit from the remote sampling system 104. The gaps or voids 802 partition a number of sample segments 804 that do not contain sufficient amounts or volume of sample for analysis by the analysis system 102. Such sample segments 804 can precede and/or follow a larger sample segment 806 having a volume (shown as $V_{SAMPLE}$) sufficient for analysis by the analysis system 102. In embodiments, the quantity of sample collected by the remote sampling system 104 (e.g., $V_{TOT}$) is adjusted to provide a sufficient amount of sample 150 for analysis by the analysis device 112. For instance, the volumetric ratio of the amount of sample 150 "pitched" to the amount of sample 150 "caught" (e.g., $V_{TOT}/V_{SAMPLE}$) is at least approximately one and one-quarter (1.25). However, this ratio is provided by way of example only and is not meant to limit the present disclosure. In some embodiments the ratio is greater than one and one-quarter, and in other embodiments the ratio is less than one and one-quarter. In one example, two and one-half milliliters (2.5 mL) of sample 150 (e.g., concentrated sulfuric acid or nitric acid) is pitched, and one milliliter (1 mL) of sample 150 is caught. In another example, one and one-half milliliters (1.5 mL) of sample 150 is pitched, and one milliliter (1 mL) of sample 150 is caught. In embodiments of the disclosure, the amount of sample 150 "pitched" is adjusted to account for the distance between the first location and the second location, the amount of sample transfer line tubing between the first location and the second location, the pressure in the sample transfer line 144, and so forth. In general, the ratio of $V_{TOT}/V_{SAMPLE}$ can be greater than one to account for the formation of the gaps/voids 802 and sample segments 804 in the sample transfer line 144 during transfer.

The system 100 can select which of a plurality of remote sampling systems 104 should transmit its respective sample to the analysis system 102 (e.g., "pitch"), whereby the detectors 126 facilitate determination of whether sufficient sample is present (e.g., $V_{SAMPLE}$ in the sample loop 164) to send to the analysis system 102 (e.g., "catch"), or whether a void or gap is present in the line (e.g., between the detectors 126), such that the sample should not be sent to the analysis system 102 at that particular time. If bubbles or gaps were to be present (e.g., in the sample loop 164), their presence could compromise the accuracy of the analysis of the sample, particularly if the sample were to be diluted or further diluted at the analysis system 102 prior to introduction to the analysis device 112, since the analysis device 112 could analyze a "blank" solution.

In some embodiments, a system 100 can be configured to determine when a continuous liquid sample segment (e.g., sample segment 806) is contained in a sample receiving line 162 and/or a sample loop 164, such that the system 100 can avoid transferring a gap or void 802 or smaller sample segment 804 to the analysis device 112. For example, the system 100 can include a first detector 126 at a first location along the sample receiving line 162 and a second detector 126 at a second location along the sample receiving line 162 (e.g., downstream from the first location). The system 100 may also include a sample loop 164 between the first detector 126 and the second detector 126. In embodiments, a valve, such as a multi-port valve switchable between at least two flow path configurations (e.g., a first flow path configuration of valve 148 shown in FIG. 3A; a second flow path configuration of valve 148 shown in FIG. 3B, etc.), can be positioned between the first detector 126 and the sample loop 164 and between the second detector 126 and the sample loop 164. In embodiments of the disclosure, the system 100 can determine that a continuous liquid sample segment is contained in the sample receiving line 162 and/or the sample loop 164 by registering liquid at both the first location and the second location at the same time, while not registering a change of state from high to low via the first detector 126 at the first location. Stated another way, the liquid sample has transferred from the first detector 126 to the second detector 126 continuously, with no change in state detected by the first detector 126 until the second detector 126 recognizes the presence of the liquid sample.

Figure 9:
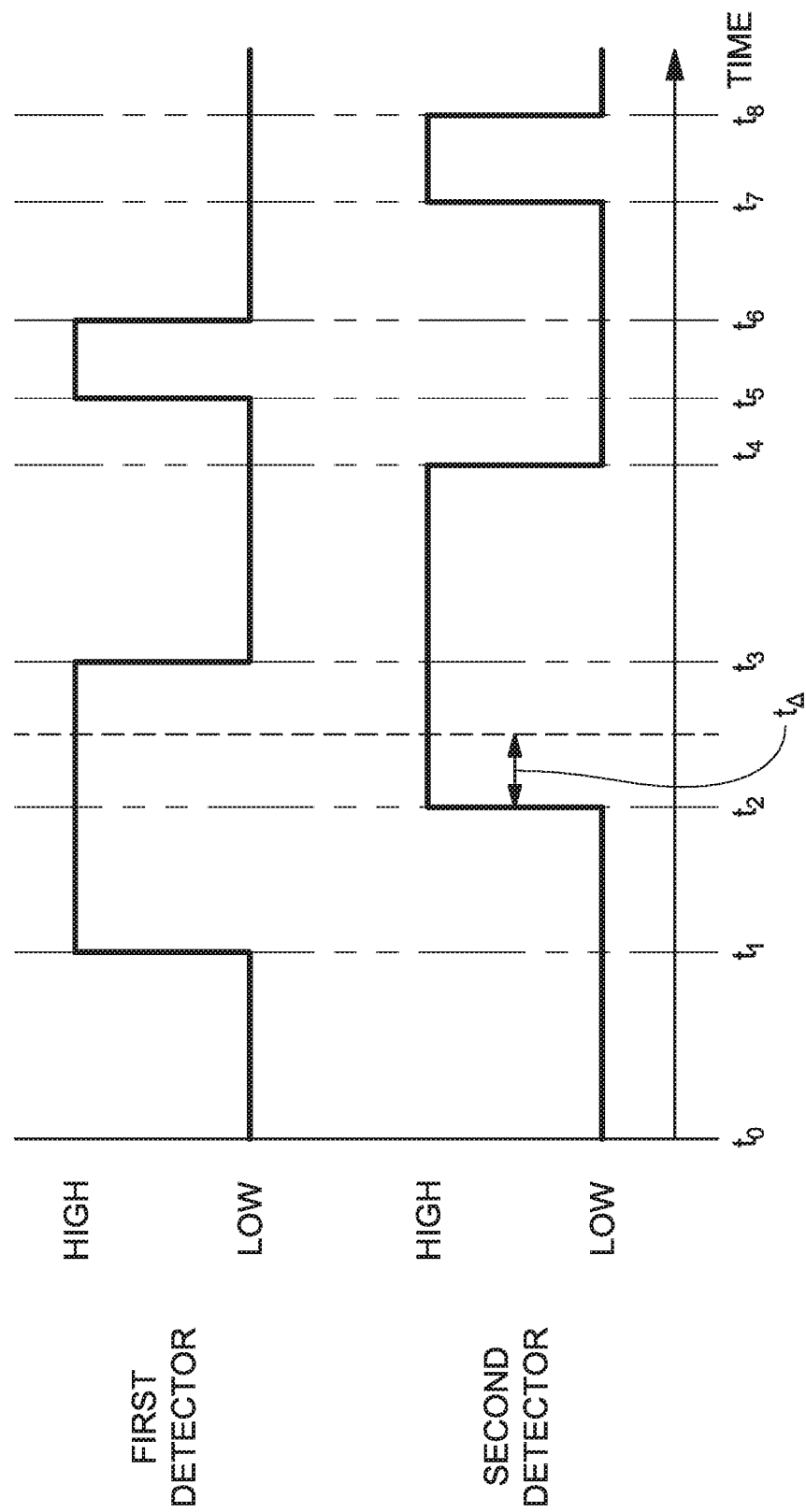
FIG. 9 is timeline illustrating multiple liquid sample segments supplied to a sample receiving line and registered by two detectors in accordance with example embodiments of the present disclosure.

In an example implementation in which two or more detectors are used to determine when a sample receiving line contains a continuous liquid segment between the detectors, a liquid segment is received in a sample receiving line. For example, with reference to FIG. 7, sample receiving line 162 receives a liquid sample segment. Then, the liquid segment is registered at a first location in the sample receiving line by initiating a detection operation using a first detector configured to detect a presence and/or an absence of the liquid segment at the first location in the sample receiving line. For example, with reference to FIG. 7, the first detector 126 detects a liquid sample segment at the first location in the sample receiving line 162 as a change of state from low to high. With reference to FIG. 9, liquid sample segments can be detected at the first location at times $t_1$ and $t_5$. Then, subsequent to registering the liquid segment at the first location, the first detector is monitored. For instance, with reference to FIG. 7, the first detector 126 is monitored by the controller 118, and the first detector 126 detects an absence of the liquid sample segment at the first location in the sample receiving line 162 as a change of state from high to low. With reference to FIG. 9, the first location is monitored (e.g., continuously, at least substantially continuously) beginning at times $t_1$ and $t_5$, and an absence of the liquid sample segments can be detected at the first location at times $t_3$ and $t_6$.

Similarly, the liquid segment is registered at a second location in the sample receiving line by initiating a detection operation using a second detector configured to detect a presence and/or an absence of the liquid segment at the second location in the sample receiving line. For instance, with reference to FIG. 7, the second detector 126 detects a liquid sample segment at the second location in the sample receiving line 162 as a change of state from low to high. With reference to FIG. 9, liquid sample segments can be detected at the second location at times $t_2$ and $t_7$. Then, subsequent to registering the liquid segment at the second location, the second detector is monitored. For instance, with reference to FIG. 7, the second detector 126 is monitored by the controller 118, and the second detector 126 detects an absence of the liquid sample segment at the second location in the sample receiving line 162 as a change of state from high to low. With reference to FIG. 9, the second location is monitored (e.g., continuously, at least substantially continuously) beginning at times $t_2$ and $t_7$, and an absence of the liquid sample segments can be detected at the second location at times $t_4$ and $t_8$.

When liquid is registered at both the first location and the second location at the same time, a continuous liquid segment is registered in the sample receiving line between the first detector and the second detector. For instance, with reference to FIG. 7, when a high state represents the presence of a liquid sample segment at each of the first detector 126 and the second detector 126, the controller 118 registers a continuous liquid sample segment in the sample receiving line 162 (e.g., as present between the first detector 126 and the second detector 126). With reference to FIG. 9, a continuous liquid sample segment can be registered at time $t_2$ when a liquid sample segment is detected at the second location.

In some embodiments, a logical AND operation can be used to determine when a continuous liquid segment is registered in the sample receiving line and initiate transfer of the continuous liquid segment from the sample receiving line to analysis equipment. For instance, with reference to FIG. 7, the controller 118 can use a logical AND operation on a high state at each of the first detector 126 and the second detector 126 and initiate a selective coupling of the sample loop 164 with the analysis device 112 using the valve 148 so that the sample loop 164 is operable to be in fluid communication with the analysis device 112 to supply the continuous liquid sample segment to the analysis device 112. In some embodiments, the controller 118 may only determine whether to switch the valve 148 to supply a continuous liquid sample segment to the analysis device 112 when a state change from low to high is registered at the first detector 126 or the second detector 126. In some embodiments, the system 100 requires that the high state at the second detector 126 is maintained for a period of time (e.g., $t_A$ shown in FIG. 9) prior to initiating selective coupling of the sample loop 164 with the analysis device. For example, a timer or timing functionality of the controller 118 and/or processor 120 can verify the period of time that the second detector 126 has maintained the high state, whereby once the second detector 126 has maintained the high state for time $t_A$ (e.g., a threshold time) and where the first detector is in the high state, the controller 118 can determine that a sufficient liquid sample segment (e.g., segment 806 in FIG. 8) has been caught, and can switch the valve 148 to supply the continuous liquid sample segment to the analysis device 112. The duration of $t_A$ can correspond to a time period beyond which it is unlikely for the second detector to be measuring a void or bubble, which can vary depending on flow rate of the sample or other transfer conditions.

In some embodiments, the controller 118 can monitor the timing of the first detector 126 at the high state and/or at the low state. For example, in embodiments where the flow characteristics of the sample being transferred from the remote sampling system 104 are known, the first detector 126 can be monitored to determine the length of time spent in the high state to approximate whether sufficient liquid sample would be present in the sample receiving line 162 and/or the sample loop 164 to cause the controller 118 to send the sample to the analysis device 112, either with or without confirmation of a high state at the second detector 126. For example, for a given flow rate of the sample, the volume of the sample can be approximated by monitoring the length of time that the first detector 126 has been in the high state. However, the flow rate of a sample may not be readily apparent due to fluctuations in pump functionality, type of sample transferred, viscosity of sample, duration of transfer, distance of transfer, ambient temperature conditions, transfer line 144 temperature conditions, or the like, so the functionality of the second detector 126 can be informative.

In embodiments of the disclosure, the systems and techniques described herein can be used to determine that a portion of a sample receiving line (e.g., a sample loop) between the first detector 126 and the second detector 126 is filled without the presence of bubbles. For example, the absence of liquid sample at the first location between times $t_3$ and $t_5$ as described with reference to FIG. 9 may correspond to the presence of a bubble in the sample receiving line 162. When the system 100 has reached a condition where no bubbles would be present in the sample receiving line 162, the controller 118 switches the valve 148 to allow the fluid in the sample loop 164 to pass to the analysis device 112 (for analysis or sample conditioning prior to analysis).

Example Method

Figure 10:
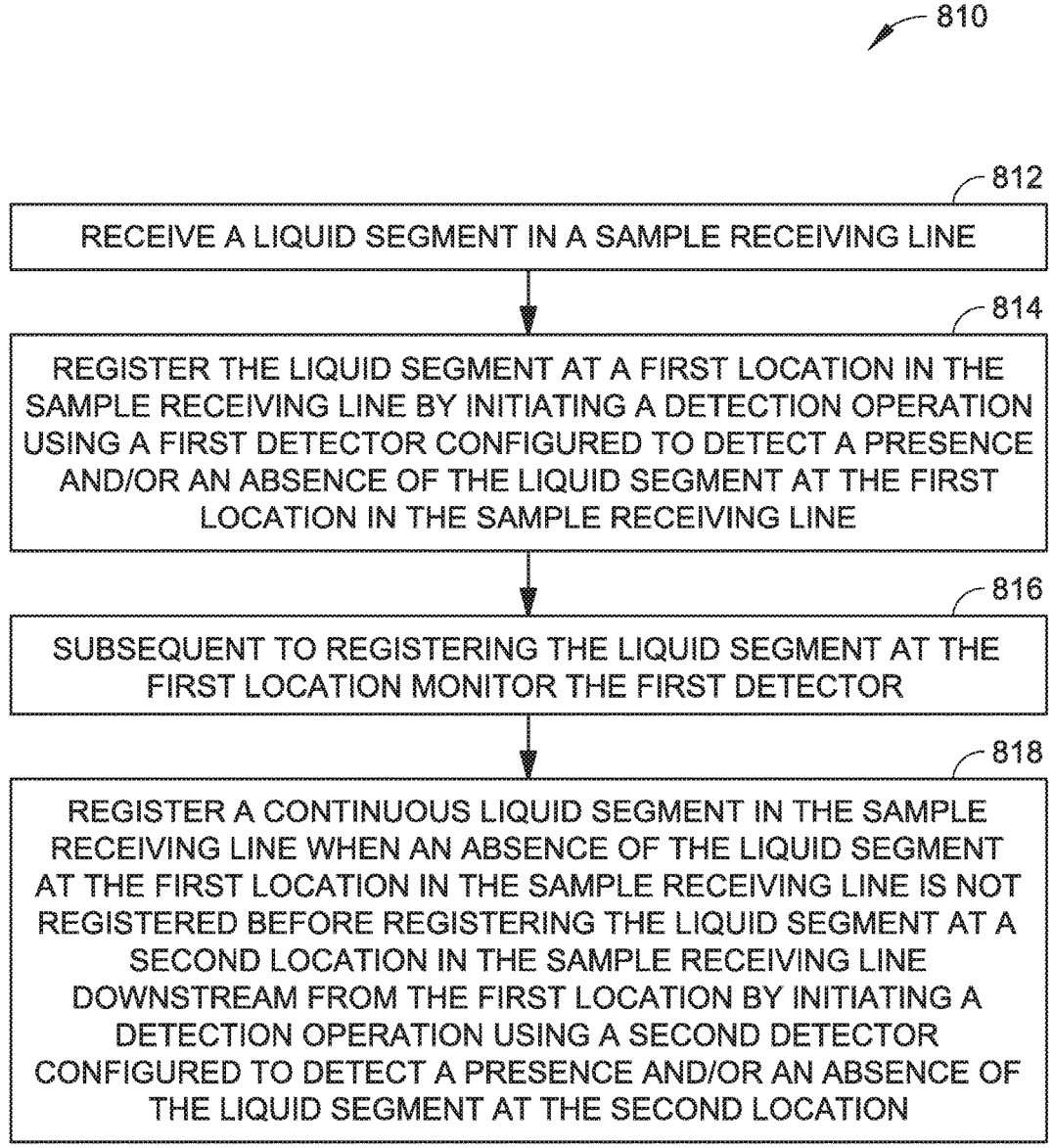
FIG. 10 is a flow diagram illustrating a method for determining when a sample receiving line contains a continuous liquid segment between detectors in accordance with example embodiments of the present disclosure.

FIG. 10 depicts a procedure 810 in an example implementation in which two detectors are used to determine when a sample receiving line contains a sufficient amount of sample in a continuous liquid sample segment for analysis by an analysis system, with no gaps or voids in the continuous liquid sample segment. As shown, a liquid segment is received in a sample receiving line (Block 812). For example, the sample receiving line 162 can receive the sample obtained by the remote sampling system 104 and transferred through transit line 144. The procedure 810 also includes registering the liquid segment at a first location in the sample receiving line with a first detector configured to detect the presence and/or absence of the liquid segment as it travels past the first location (Block 814). For example, the first detector 126 can measure the presence of the liquid sample segment at the first location in the sample receiving line 162. With reference to FIG. 9, liquid sample segments are detected at the first location at times $t_1$ and $t_5$.

Next, subsequent to registering the liquid segment at the first location, the first detector is monitored (Block 816). For instance, the first detector 126 can be monitored by the controller 118 to determine whether there is an absence of the liquid segment at the first location in the sample receiving line 162 (e.g., whether the first detector 126 has transitioned from a high state, indicating detection of sample fluid, to a low state, wherein no sample fluid is detected). With reference to FIG. 9, the first location is monitored (e.g., continuously, at least substantially continuously) beginning at times $t_1$ and $t_5$. Then, a continuous liquid segment is registered in the sample receiving line when an absence of the liquid segment at the first location in the sample receiving line is not registered before registering the liquid segment at a second location in the sample receiving line downstream from the first location by performing a detection operation using a second detector configured to detect a presence and/or an absence of the liquid segment at the second location (Block 818). For example, with reference to FIG. 9, the first detector 126 detects the presence of the sample fluid at times $t_1$ and $t_5$, whereas the second detector 126 detects the presence of the sample fluid at times $t_2$ and $t_7$. Only the liquid sample segment between times $t_1$ and $t_3$ at the first detector would be registered by the second detector (beginning at time $t_2$) without the first detector 126 detecting an absence in the interim time before the second detector detected that sample segment. At such time, the controller 118 could directed the valve 148 to switch to send the sample contained in the sample loop 164 to the analysis device 112. While the first detector 126 registers the presence of the liquid sample at $t_5$, the first detector also detects the absence of the liquid sample at $t_6$, before the second detector 126 subsequently detects the presence of the liquid sample at $t_7$. As such, the system 100 will recognize that a gap or void (e.g., gap/void 802) is present in the sample loop 164 and will not switch the valve 148 for analysis, instead allowing the inadequate sample segment (e.g., liquid segment 804) to pass to waste. As described herein, a timer (e.g., implemented by the controller 118) can be used to cause the valve 148 to switch once the second detector 126 has maintained the high state for a certain period of time (e.g., $t_A$) after the first detector 126 has maintained the high state in the interim.

Control Systems

A system 100, including some or all of its components, can operate under computer control. For example, a processor 120 can be included with or in a system 100 to control the components and functions of systems described herein using software, firmware, hardware (e.g., fixed logic circuitry), manual processing, or a combination thereof. The terms "controller," "functionality," "service," and "logic" as used herein generally represent software, firmware, hardware, or a combination of software, firmware, or hardware in conjunction with controlling the systems. In the case of a software implementation, the module, functionality, or logic represents program code that performs specified tasks when executed on a processor (e.g., central processing unit (CPU) or CPUs). The program code can be stored in one or more computer-readable memory devices (e.g., internal memory and/or one or more tangible media), and so on. The structures, functions, approaches, and techniques described herein can be implemented on a variety of commercial computing platforms having a variety of processors.

For instance, one or more components of the system, such as the analysis system 102, remote sampling system 104, valves 148, pumps, and/or detectors (e.g., the first detector 126, the second detector 126, the sample detector 130) can be coupled with a controller for controlling the collection, delivery, and/or analysis of samples 150. For example, the controller 118 can be configured to switch a valve 148 coupling the sample loop 164 to the analysis system 102 and direct a sample 150 from the sample loop 164 to the analysis system 102 when a successful "catch" is indicated by the first detector 126 and the second detector 126 (e.g., when both sensors detect liquid). Furthermore, the controller 118 can implement functionality to determine an "unsuccessful catch" (e.g., when the sample loop 164 is not filled with enough of a sample 150 for a complete analysis by the analysis system 102). In some embodiments, an "unsuccessful catch" is determined based upon, for instance, variations in the signal intensity of a signal received from a sensor, such as the first detector 126 or the second detector 126. In other embodiments, an "unsuccessful catch" is determined when the first detector 126 has indicated a sample 150 in the sample receiving line 162 and a predetermined amount of time had passed in which the second detector 126 has not indicated a sample 150 in the sample receiving line 162.

In some embodiments, the controller 118 is communicatively coupled with an indicator at a remote location, such as the second location, and provides an indication (e.g., an alert) at the second location when insufficient sample 150 is received at the first location. The indication can be used to initiate (e.g., automatically) additional sample collection and delivery. In some embodiments, the indicator provides an alert to an operator (e.g., via one or more indicator lights, via a display readout, a combination thereof, etc.). Further, the indication can be timed and/or initiated based upon a one or more predetermined conditions (e.g., only when multiple samples have been missed). In some embodiments, an indicator can also be activated based upon conditions measured at a remote sampling site. For instance, a detector 130 at the second location can be used to determine when sample 150 is being provided to a remote sampling system 104, and the indicator can be activated when sample 150 is not being collected.

Figure 11:
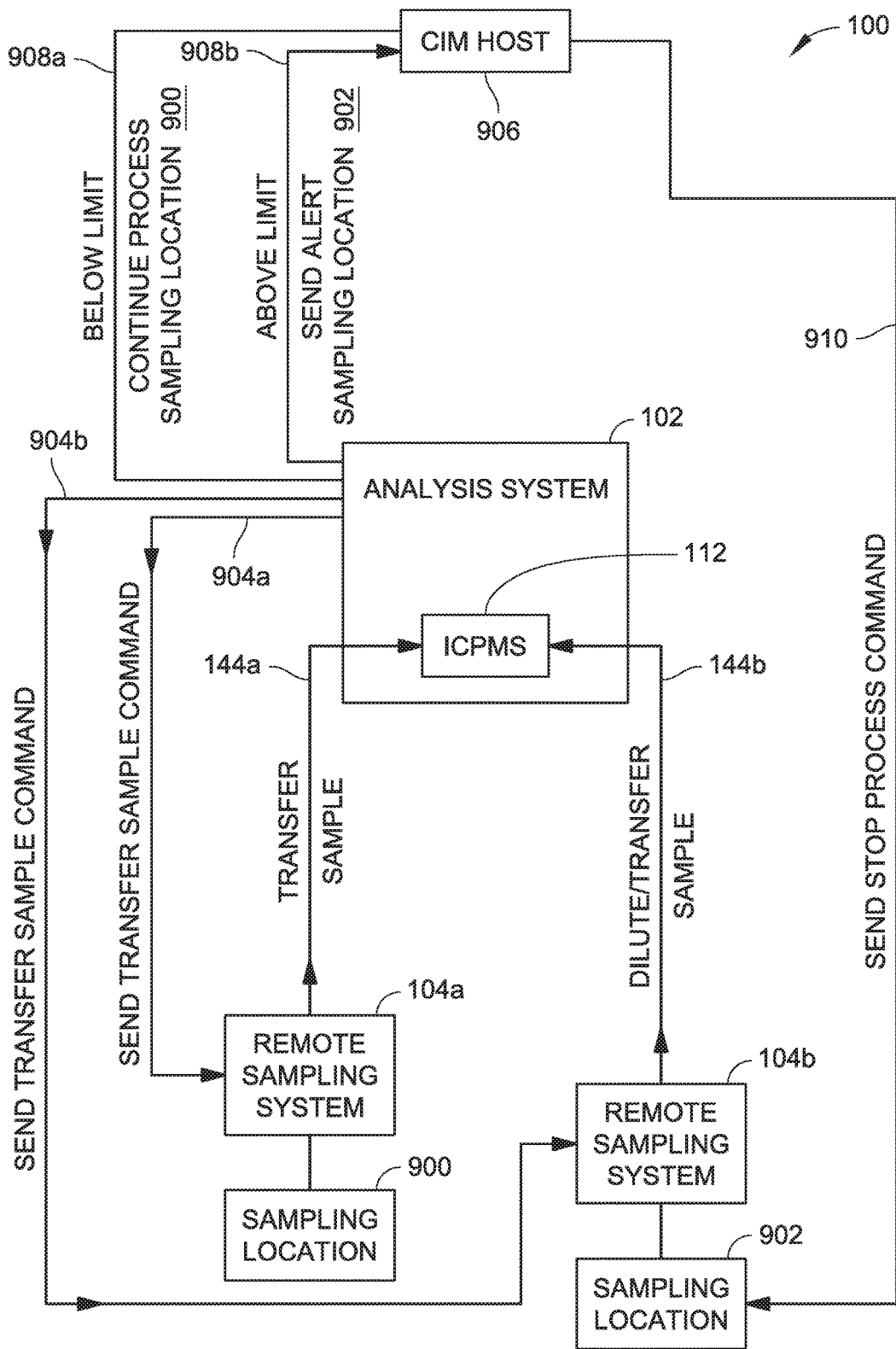
FIG. 11 is a process flow diagram of a control system for monitoring and controlling process operations based on chemical detection limits in accordance with example embodiments of the present disclosure.
Figure 12:
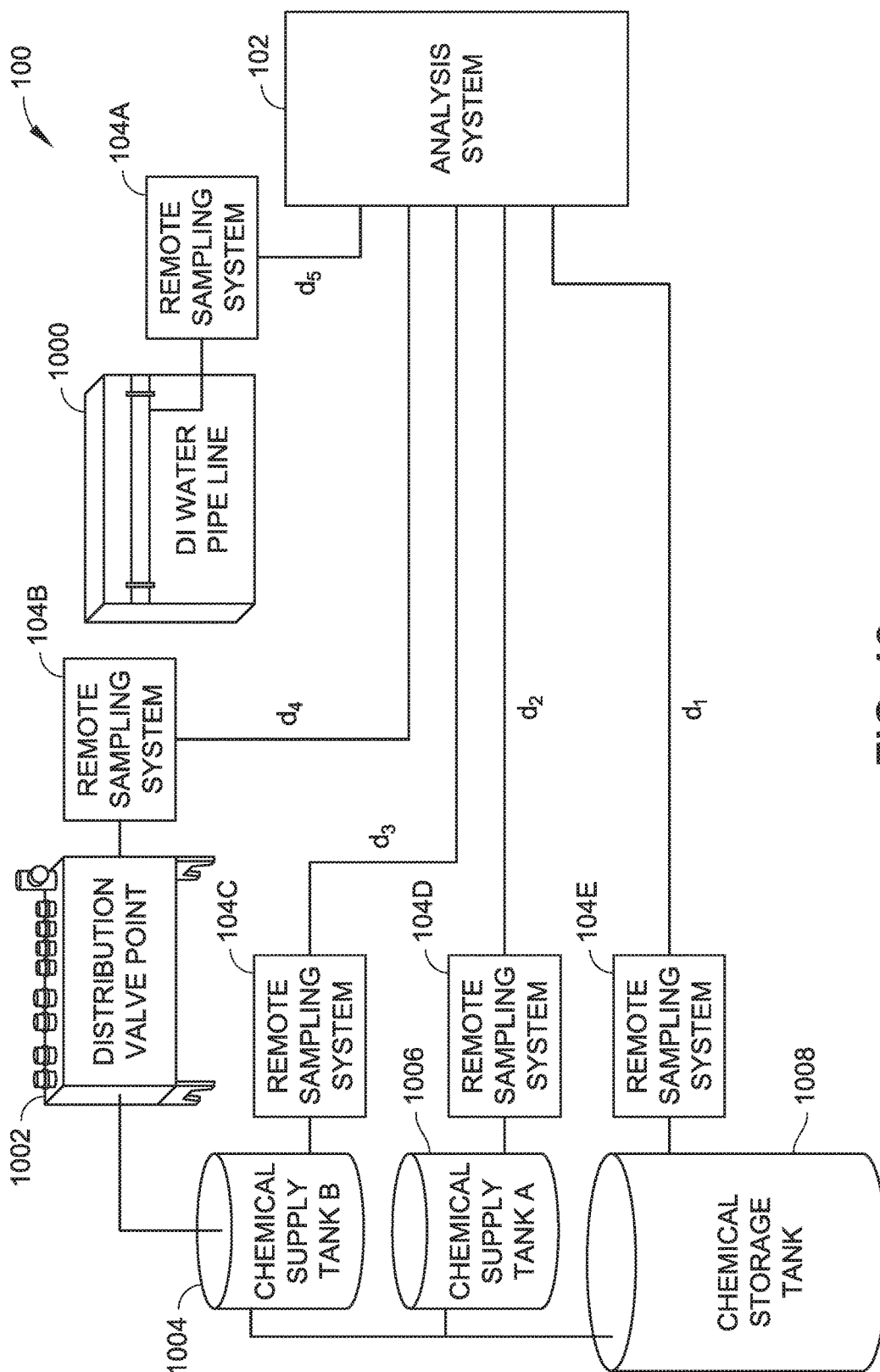
FIG. 12 is a schematic diagram of a processing facility incorporating a plurality of remote sampling systems in accordance with example embodiments of the present disclosure.

In some embodiments, the controller 118 is operable to provide different timing for the collection of samples from different remote locations, and/or for different types of samples 150. For example, the controller 118 can be alerted when a remote sampling system 104 is ready to deliver a sample 150 to the sample transfer line 144, and can initiate transfer of the sample 150 into the sample transfer line 144. The controller 118 can also be communicatively coupled with one or more remote sampling systems 102 to receive (and possibly log/record) identifying information associated with samples 150, and/or to control the order that samples 150 are delivered within the system 100. For example, the controller 118 can remotely queue multiple samples 150 and coordinate their delivery through one or more of the sample transfer lines 144. In this manner, delivery of samples 150 can be coordinated along multiple simultaneous flow paths (e.g., through multiple sample transfer lines 144), one or more samples 150 can be in transfer while one or more additional samples 150 are being taken, and so on. For example, FIG. 11 shows an example control flow diagram for system 100, where the analysis system 102 is shown in fluid communication with two remote sample locations, shown as sample location 900 and sample location 902, via two remote sampling systems 104*a* and 104*b* and associated transfer lines 144*a* and 144*b*. In the embodiment shown, the analysis system 102 sends commands to each of the remote sampling system 104*a* and the remote sampling system 104*b*, shown as 904*a* and 904*b*, respectively. The remote sampling system 104*a* and the remote sampling system 104*b* each transfer the sample obtained at the respective sampling location (sampling location 900 for remote sampling system 104*a*, sampling location 902 for remote sampling system 104*b*) to the analysis system 102 via transfer line 144*a* and transfer line 144*b*, respectively. The analysis system 102 then processes the samples to determine amounts of various chemical species container therein. The analysis system 102 then determines whether any of the amounts of the chemical species exceeds an element-specific limit (e.g., a limit for a specific contaminant in the sample). In embodiments, the system 100 can set contamination limits independently for each sampling location and for particular chemical species at each sampling location independently. For example, the tolerance for a particular metal contaminant may decrease during processing, so downstream chemical samples may have lower limits for the particular chemical species than for chemical samples taken upstream. As shown in FIG. 11, the analysis system 102 determined that no chemical species exceeds any of the element-specific limits for the sample obtained at sampling location 900 by the remote sampling system 104*a*. The analysis system 102 then sends a CIM Host 906 an indication, shown as 908*a*, to permit continuation of process applications at the sampling location 900 due to operation of the process applications below the element-specific limits. The analysis system 102 has determined that at least one of the chemical species present in the sample obtained at sampling location 902 by the remote sampling system 104*b* exceeds the element-specific limit (e.g., a limit for a contaminant in the sample). The analysis system 102 then sends the CIM Host 906 an indication, shown as 908*b*, to send an alert directed to the process applications at the sampling location 902 due to operation of the process applications above the element-specific limits. The CIM Host 906 then directs, via a stop process command 910, the processes at the sampling location 902 to stop operation based upon the analysis of the sample obtained by the remote sampling system 104*b* at the sampling location 902. In embodiments, communication between the CIM Host 906 and the components of the system 100 can be facilitated by the SECS/GEM protocol. In embodiments, the system 100 can include context-specific actions when an element is determined to be above an element-specific limit in a sample for a particular sample location, where such context-specific actions can include, but are not limited to, ignoring an alert and continuing the process operation, stopping the process operation, running a system calibration and then re-running the over-limit sample, or the like. For example, upon a first alert, the analysis system 102 can perform a calibration (or another calibration) and then re-run the sample, whereas a subsequent alert (e.g., a second alert) would cause the CIM Host 906 to command the processes at the offending sampling location to halt operations.

The controller 118 can include a processor 120, a memory 122, and a communications interface 124. The processor 120 provides processing functionality for the controller 118 and can include any number of processors, micro-controllers, or other processing systems, and resident or external memory for storing data and other information accessed or generated by the controller 118. The processor 120 can execute one or more software programs that implement techniques described herein. The processor 120 is not limited by the materials from which it is formed or the processing mechanisms employed therein and, as such, can be implemented via semiconductor(s) and/or transistors (e.g., using electronic integrated circuit (IC) components), and so forth.

The memory 122 is an example of tangible, computer-readable storage medium that provides storage functionality to store various data associated with operation of the controller 118, such as software programs and/or code segments, or other data to instruct the processor 120, and possibly other components of the controller 118, to perform the functionality described herein. Thus, the memory 122 can store data, such as a program of instructions for operating the system 100 (including its components), and so forth. It should be noted that while a single memory is described, a wide variety of types and combinations of memory (e.g., tangible, non-transitory memory) can be employed. The memory 122 can be integral with the processor 120, can comprise stand-alone memory, or can be a combination of both.

The memory 122 can include, but is not necessarily limited to: removable and non-removable memory components, such as random-access memory (RAM), read-only memory (ROM), flash memory (e.g., a secure digital (SD) memory card, a mini-SD memory card, and/or a micro-SD memory card), magnetic memory, optical memory, universal serial bus (USB) memory devices, hard disk memory, external memory, and so forth. In implementations, the system 100 and/or the memory 122 can include removable integrated circuit card (ICC) memory, such as memory 122 provided by a subscriber identity module (SIM) card, a universal subscriber identity module (USIM) card, a universal integrated circuit card (UICC), and so on.

The communications interface 124 is operatively configured to communicate with components of the system. For example, the communications interface 124 can be configured to transmit data for storage in the system 100, retrieve data from storage in the system 100, and so forth. The communications interface 124 is also communicatively coupled with the processor 120 to facilitate data transfer between components of the system 100 and the processor 120 (e.g., for communicating inputs to the processor 120 received from a device communicatively coupled with the controller 118). It should be noted that while the communications interface 124 is described as a component of a controller 118, one or more components of the communications interface 124 can be implemented as external components communicatively coupled to the system 100 via a wired and/or wireless connection. The system 100 can also comprise and/or connect to one or more input/output (I/O) devices (e.g., via the communications interface 124), including, but not necessarily limited to: a display, a mouse, a touchpad, a keyboard, and so on.

The communications interface 124 and/or the processor 120 can be configured to communicate with a variety of different networks, including, but not necessarily limited to: a wide-area cellular telephone network, such as a 3G cellular network, a 4G cellular network, or a global system for mobile communications (GSM) network; a wireless computer communications network, such as a Wi-Fi network (e.g., a wireless local area network (WLAN) operated using IEEE 802.11 network standards); an internet; the Internet; a wide area network (WAN); a local area network (LAN); a personal area network (PAN) (e.g., a wireless personal area network (WPAN) operated using IEEE 802.15 network standards); a public telephone network; an extranet; an intranet; and so on. However, this list is provided by way of example only and is not meant to limit the present disclosure. Further, the communications interface 124 can be configured to communicate with a single network or multiple networks across different access points.

EXAMPLE 1

Example Monitoring System

Generally, the systems 100 described herein can incorporate any number of remote sampling systems 104 to take samples from any number of sampling locations. In an implementation, shown in FIG. 12, the system 100 includes five remote sampling systems 104 (shown as 104A, 104B, 104C, 104D, 104E) positioned at five different locations of a process facility utilizing chemical baths, bulk chemicals, environmental effluents, and other liquid samples. The remote sampling systems 104 acquire samples at the different locations to transfer to the analysis system 102 positioned remotely from each of the five remote sampling systems 104. A first remote sampling system 104A is positioned proximate a deionized water pipeline 1000 and spaced from the analysis system 102 by a distance (shown as $d_5$) of approximately forty meters (40 m). A second remote sampling system 104B is positioned proximate a distribution valve point 1002 and spaced from the analysis system 102 by a distance (shown as $d_4$) of approximately eighty meters (80 m). A third remote sampling system 104C is positioned proximate a chemical supply tank 1004 and spaced from the analysis system 102 by a distance (shown as $d_3$) of approximately eighty meters (80 m). The chemical supply tank 1004 is positioned remotely from, and supplied with chemical from, a chemical storage tank 1008. A fourth remote sampling system 104D is positioned proximate a chemical supply tank 1006 and spaced from the analysis system 102 by a distance (shown as $d_2$) of approximately eighty meters (80 m). The chemical supply tank 1006 is positioned remotely from, and supplied with chemical from, the chemical storage tank 1008. A fifth remote sampling system 104E is positioned proximate the chemical storage tank 1004 and spaced from the analysis system 102 by a distance (shown as $d_1$) of approximately three hundred meters (300 m). While five remote sampling systems 104 are shown, the system 100 can utilize more than five remote sampling systems 104 to monitor ultra-trace impurities throughout the processing facility, such as at other process streams, chemical baths, bulk chemical storage, environmental effluents, and other liquid samples. In an implementation, the transfer of sample from the remote sampling systems 104 to the analysis system is provided at a rate of approximately 1.2 meters per second (1.2 m/s), providing near real-time analysis (e.g., ICPMS analysis) of the ultra-trace impurities throughout the processing facility.

EXAMPLE 2

Reproducibility

In an implementation, the analysis system 102 was positioned one hundred meters (100 m) from a remote sampling system 104. The remote sampling system 104 obtained twenty discrete samples and transported them to the analysis system 102 for determination of the signal intensity of each chemical specie present in each of the twenty discrete samples. Each discrete sample included the following chemical species: Lithium (Li), Beryllium (Be), Boron (B), Sodium (Na), Magnesium (Mg), Aluminum (Al), Calcium (Ca), Manganese (Mn), Iron (Fe), Cobalt (Co), Nickel (Ni), Copper (Cu), Zinc (Zn), Germanium (Ge), Strontium (Sr), Silver (Ag), Cadmium (Cd), Indium (In), Tin (Sn), Antimony (Sb), Barium (Ba), Cerium (Ce), Hafnium (Hf), Tungsten (W), and Lead (Pb). Upon analysis by the analysis system 102, it was determined that the relative standard deviation (RSD) was less than three percent (<3%) across all twenty discrete samples for all chemical species. Accordingly, the example system 100 at one hundred meters between the analysis system 102 and the remote sampling system 104 provided reliable reproducibility from obtaining the sample, transferring the sample one hundred meters to the analysis system 102 (e.g., via transfer line 144), and analyzing the samples with the analysis system 102.

EXAMPLE 3

Comparison with Manual
Sampling—Semiconductor Process Example

Figure 13:
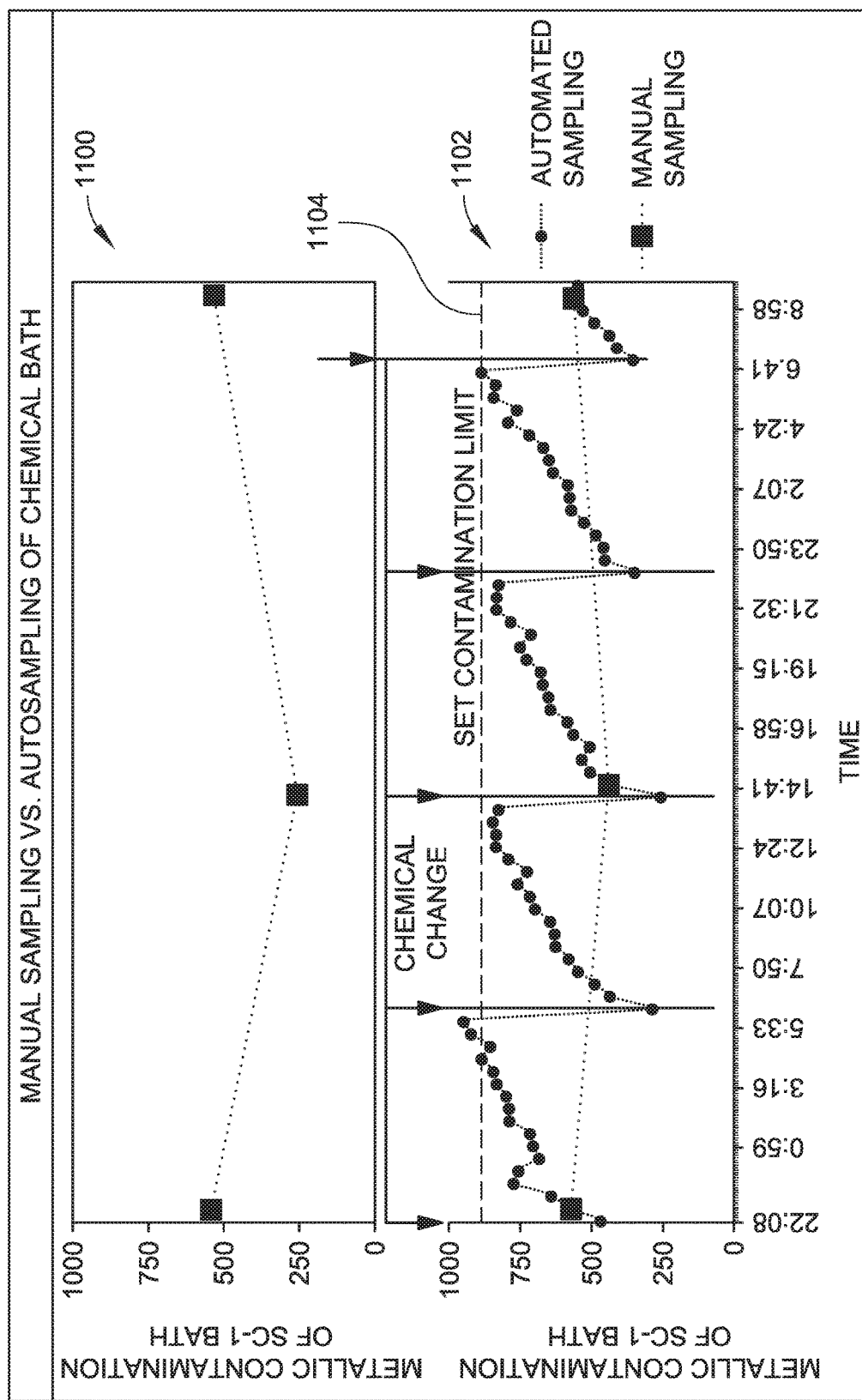
FIG. 13 is a chart illustrating metallic contamination of a chemical bath over time, with data points representing manual sampling and data points obtained with an automatic system in accordance with example embodiments of the present disclosure.

Referring to FIG. 13, a chart showing metallic contamination of a chemical bath for semiconductor manufacturing processes (SC-1 bath) over time is provided. The chart includes a portion 1100 showing data points for metallic contamination measured from manual samples taken at three points in time. The chart also includes a portion 1102 showing the data points for metallic contamination measured from manual samples from portion 1100 superimposed on data points for metallic contamination measured from samples taken from the system 100 (e.g., from the remote sampling systems 104) at a sampling frequency exceeding that of the manual sampling method (e.g., at least sixteen to seventeen times more frequently). As shown in portion 1102, a gradual increase in contaminants occurs over time in the semiconductor manufacturing process. Life time or life counts methods of determining when to exchange the chemicals in a particular semiconductor process (e.g., the manual sampling technique from portion 1100) are often unable to account for the particularities of the metallic contamination over time. As such, the chemicals are often exchanged without knowledge of the metal contaminants in the bath. This can result in over-exchanging, where the chemical bath could actually provide additional wafer processing but is changed out anyway (e.g., resulting in loss of process uptime), or in under-exchanging, where the chemical bath actually has an unacceptable metallic contamination but is not changed out until a later time (e.g., potentially jeopardizing the wafers produced by the process). As can be seen in portion 1102, the metallic contamination can be tracked with the system 100 at a higher frequency automatically. A contamination limit 1104 is set to alert the CIM Host 906 when the contaminant limit is reached for the chemical bath. The system 100 can therefore automatically cause a stop in process operations when the contamination limit 1104 is reached (e.g., avoiding under-exchanging), while allowing the process to continue when the contamination limit 1104 is not reached, thereby providing process uptime when feasible (e.g., avoiding over-exchanging).

CONCLUSION

In implementations, a variety of analytical devices can make use of the structures, techniques, approaches, and so on described herein. Thus, although systems are described herein, a variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

Generally, any of the functions described herein can be implemented using hardware (e.g., fixed logic circuitry such as integrated circuits), software, firmware, manual processing, or a combination thereof. Thus, the blocks discussed in the above disclosure generally represent hardware (e.g., fixed logic circuitry such as integrated circuits), software, firmware, or a combination thereof. In the instance of a hardware configuration, the various blocks discussed in the above disclosure may be implemented as integrated circuits along with other functionality. Such integrated circuits may include all of the functions of a given block, system, or circuit, or a portion of the functions of the block, system, or circuit. Further, elements of the blocks, systems, or circuits may be implemented across multiple integrated circuits. Such integrated circuits may comprise various integrated circuits, including, but not necessarily limited to: a monolithic integrated circuit, a flip chip integrated circuit, a multichip module integrated circuit, and/or a mixed signal integrated circuit. In the instance of a software implementation, the various blocks discussed in the above disclosure represent executable instructions (e.g., program code) that perform specified tasks when executed on a processor. These executable instructions can be stored in one or more tangible computer readable media. In some such instances, the entire system, block, or circuit may be implemented using its software or firmware equivalent. In other instances, one part of a given system, block, or circuit may be implemented in software or firmware, while other parts are implemented in hardware.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A system comprising:
   a sample receiving line configured to receive a liquid segment;
   a first detector configured to detect at least one of a presence or an absence of the liquid segment at a first location in the sample receiving line, the first detector configured to register the absence of the liquid segment at the first location in the sample receiving line as a first state, and register the presence of the liquid segment at the first location in the sample receiving line as a second state;
   a second detector configured to detect at least one of a presence or an absence of the liquid segment at a second location in the sample receiving line downstream from the first location, the second detector configured to register the absence of the liquid segment at the second location in the sample receiving line as a first state, and register the presence of the liquid segment at the second location in the sample receiving line as a second state;
   a valve coupled between the first location in the sample receiving line and the second location in the sample receiving line, the valve switchable between at least two flow path configurations;
   a controller communicatively coupled with the first detector and the second detector, the controller configured to register a continuous liquid segment in the sample receiving line when the first detector is in the second state and the second detector is at the second state prior to the controller registering a change of state of the first detector from the second state to the first state;
   an analysis system at the first location;
   a remote sampling system at the second location remote from the first location, the remote sampling system configured to receive the liquid segment for analysis; and
   a sample transfer line configured to transport the liquid segment from the second location to the first location, the sample transfer line coupled with the remote sampling system so that the remote sampling system is operable to be in fluid communication with the sample transfer line for driving the liquid segment to the first location, wherein the analysis system includes the sample receiving line, and the sample receiving line is configured to selectively couple with the sample transfer line and the analysis system so that the sample receiving line is operable to be in fluid communication with the sample transfer line to receive the liquid segment and in fluid communication with the analysis system to supply the continuous liquid segment to the analysis system.

2. The system of claim 1, further comprising a timer configured to monitor a time at which the second detector maintains the second state, wherein the controller is configured to register the continuous liquid segment in the sample receiving line when each of (i) the first detector is in the second state and the second detector is at the second state prior to the controller registering a change of state of the first detector from the second state to the first state and (ii) the time at which the second detector maintains the second state exceeds a threshold time.

3. The system of claim 1, wherein the controller is configured to switch the valve between the at least two flow path configurations responsive to registering the continuous liquid segment in the sample receiving line.

4. The system of claim 1, wherein a volumetric ratio of the liquid segment to the continuous liquid segment is greater than one.

5. The system of claim 1, wherein the sample transfer line is at least five meters in length.

6. The system of claim 1, wherein the sample transfer line is at least ten meters in length.

7. The system of claim 1, wherein the sample transfer line is at least thirty meters in length.

8. The system of claim 1, wherein the analysis system includes a plurality of analysis devices.

9. The system of claim 8, wherein the plurality of analysis devices includes at least two of a mass spectrometer, an optical emission spectrometer, an ion chromatograph, a liquid chromatograph, a Fourier transform infrared spectrometer, a particle counter, a moisture analyzer, and a gas chromatograph.

10. A system comprising:
a sample receiving line configured to receive a liquid segment the sample receiving line including a sample loop;
a first detector configured to detect at least one of a presence or an absence of the liquid segment at a first location in the sample receiving line, the first detector configured to register the absence of the liquid segment at the first location in the sample receiving line as a first state, and register the presence of the liquid segment at the first location in the sample receiving line as a second state;
a second detector configured to detect at least one of a presence or an absence of the liquid segment at a second location in the sample receiving line downstream from the first location, the second detector configured to register the absence of the liquid segment at the second location in the sample receiving line as a first state, and register the presence of the liquid segment at the second location in the sample receiving line as a second state; and
a controller communicatively coupled with the first detector and the second detector, the controller configured to register a continuous liquid segment in the sample receiving line when the first detector is in the second state and the second detector is at the second state prior to the controller registering a change of state of the first detector from the second state to the first state, the controller further configured to determine whether the continuous liquid segment includes a chemical component that exceeds an element-specific contamination limit.

11. A method comprising
receiving a liquid segment in a sample receiving line;
registering a first state with a first detector responsive to detection of the liquid segment at a first location in the sample receiving line with the first detector, the first state of the first detector corresponding to a presence of the liquid segment at the first location;
registering a first state with a second detector responsive to detection of the liquid segment at a second location in the sample receiving line downstream from the first location, the first state of the second detector corresponding to a presence of the liquid segment at the second location;
monitoring whether the second detector registered the first state prior to the first detector registering a second state, the second state corresponding to an absence of the liquid segment at the first location;
registering a continuous liquid segment in the sample receiving line when the second detector registered the first state prior to the first detector registering a second state;
monitoring a time at which the second detector maintains the first state; and
transferring the continuous liquid segment from the sample receiving line to an analysis system responsive to registering the continuous liquid segment in the sample receiving line, the step of transferring the continuous liquid segment from the sample receiving line to an analysis system responsive to registering the continuous liquid segment in the sample receiving line including at least one of:
automatically switching a valve from a first flow path configuration to a second flow path configuration to transfer the continuous liquid segment from the sample receiving line to the analysis system responsive to registering the continuous liquid segment in the sample receiving line; or
transferring the continuous liquid segment from the sample receiving line to a plurality of analysis devices responsive to registering the continuous liquid segment in the sample receiving line.

12. The method of claim 11, wherein transferring the continuous liquid segment from the sample receiving line to an analysis system responsive to registering the continuous liquid segment in the sample receiving line includes:
automatically switching a valve from a first flow path configuration to a second flow path configuration to transfer the continuous liquid segment from the sample receiving line to the analysis system responsive to registering the continuous liquid segment in the sample receiving line.

13. The method of claim 11, wherein transferring the continuous liquid segment from the sample receiving line to an analysis system responsive to registering the continuous liquid segment in the sample receiving line includes:
transferring the continuous liquid segment from the sample receiving line to a plurality of analysis devices responsive to registering the continuous liquid segment in the sample receiving line.

14. The method of claim 11, wherein registering a continuous liquid segment in the sample receiving line when the second detector registered the first state prior to the first detector registering a second state includes:
registering a continuous liquid segment in the sample receiving line when each of (i) the second detector registered the first state prior to the first detector registering a second state and (ii) the time at which the second detector maintains the second state exceeds a threshold time.

15. The method of claim 11, further comprising:
determining whether the continuous liquid segment includes a chemical component that exceeds an element-specific contamination limit.

16. The method of claim 15, further comprising:
automatically sending an alert to an origin location of the liquid segment when the continuous liquid segment is determined to include the chemical component that exceeds the element-specific contamination limit.

\* \* \* \* \*